(12) United States Patent
Chen et al.

(10) Patent No.: US 9,681,647 B2
(45) Date of Patent: Jun. 20, 2017

(54) MAMMAL WITH AN ORTHOTOPIC TUMOR CAPABLE OF METASTASIS, A METHOD OF MAKING AND A METHOD OF USING

(71) Applicant: Cornell University, Ithaca, NY (US)

(72) Inventors: Huanhuan Chen, Flushing, NY (US); Steven M. Lipkin, Scarsdale, NY (US); Xiling Shen, Ithaca, NY (US)

(73) Assignee: Cornell University, Ithaca, NY (US)

(*) Notice: Subject to any disclaimer, the term of this patent is extended or adjusted under 35 U.S.C. 154(b) by 27 days.

(21) Appl. No.: 14/412,312

(22) PCT Filed: Jul. 3, 2013

(86) PCT No.: PCT/US2013/049302
§ 371 (c)(1),
(2) Date: Dec. 31, 2014

(87) PCT Pub. No.: WO2014/008385
PCT Pub. Date: Jan. 9, 2014

(65) Prior Publication Data
US 2015/0164053 A1 Jun. 18, 2015

Related U.S. Application Data

(60) Provisional application No. 61/668,289, filed on Jul. 5, 2012.

(51) Int. Cl.
*A01K 67/027* (2006.01)
*C12N 15/00* (2006.01)
*C07K 14/715* (2006.01)
*C12N 15/113* (2010.01)
*A61K 49/00* (2006.01)

(52) U.S. Cl.
CPC ...... *A01K 67/0278* (2013.01); *A01K 67/0271* (2013.01); *A61K 49/0008* (2013.01); *C07K 14/7158* (2013.01); *C12N 15/1138* (2013.01); *A01K 2207/12* (2013.01); *A01K 2227/105* (2013.01); *A01K 2267/0331* (2013.01); *C12N 2310/14* (2013.01); *C12N 2310/531* (2013.01); *C12N 2740/15043* (2013.01); *C12N 2830/003* (2013.01)

(58) Field of Classification Search
USPC ............................ 424/93.21; 800/8, 18, 21, 3
See application file for complete search history.

(56) References Cited

U.S. PATENT DOCUMENTS

| | | | |
|---|---|---|---|
| 7,227,035 B2 * | 6/2007 | Ungashe | A61K 31/18 564/84 |
| 8,367,052 B2 | 2/2013 | Han et al. | |
| 9,233,120 B2 * | 1/2016 | Lillard | A61K 31/7088 |
| 2008/0089950 A1 | 4/2008 | Chen et al. | |
| 2012/0034157 A1 | 2/2012 | Hyde et al. | |
| 2012/0100154 A1 * | 4/2012 | Lillard | A61K 31/7088 424/158.1 |

FOREIGN PATENT DOCUMENTS

| | | |
|---|---|---|
| KR | 10-2013-0002100 A | 1/2013 |
| WO | 98/11218 A1 | 3/1998 |
| WO | 2008/028692 A2 | 3/2008 |

OTHER PUBLICATIONS

Ding (J. Clin. Invest., 2011, vol. 121, No. 11, p. 4526-4536).*
Chen, H.J., et al., Chemokine 25-induced signaling suppresses colon cancer invasion and metastasis, The Journal of Clinical Investigation, Aug. 6, 2012, vol. 122, No. 9, pp. 3184-3196.
Ding, Q, et al., APOBEC3G promotes liver metastasis in an orthotopic mouse model of colorectal cancer and predicts human hepatic metastasis, The Journal of Clinical Investigation, Oct. 10, 2011, vol. 121, No. 11, pp. 4526-4536.
Meier, R. et al., The Chemokine Receptor CXCR4 Strongly Promotes Neuroblastoma Primary Tumour and Metastatic Growth, but not Invasion, Plos One, Oct. 10, 2007, vol. 2, No. 10, e1016, pp. 1-10.
Amersi, F.F., et al., Activation of CCR9/CCL25 in Cutaneous Melanoma Medaites Preferential Metastasis to the Small Intestine, Clinical Cancer Research, Human Cancer Biology, Feb. 1, 2008, vol. 14, No. 3, pp. 638-645.
Lee, Y., et al., Mesenchymal stem cells regulate the proliferation of T cells via the growth-related oncogene/CXC chemokine receptor, CXCR2, Cellular Immunology, Sep. 5, 2012, vol. 279, pp. 1-11.
Sung, H.J., et al., Human LZIP induces monocyte CC chemokine receptor 2 expression leading to enhancement of monocyte chemoattractant protein 1/CCL2-induced cell migration, Experimental and Molecular Medicine, Jun. 2008, vol. 40, No. 3, pp. 332-338.
Darash-Yahana, M., et al., Role of high expression levels of CXCR4 in tumor growth, vascularization, and metastasis, The FASEB Journal—official publication of the Federation of American Societies for Experimental Biology, Aug. 2004, vol. 18, No. 11, pp. 1240-1242.
Vianello, F., et al., Murine B16 Melanomas Expressing high Levels of the Chemokine Stromal-Derived Factor-1/CXCL12 Induce Tumor-Specific T Cell Chemorepulsion and Escape from Immune Control, The Journal of Immunology, 2006, vol. 176, pp. 2902-2914.

(Continued)

*Primary Examiner* — Michael Wilson
(74) *Attorney, Agent, or Firm* — Hodgson Russ LLP

(57) ABSTRACT

Provided are compositions and methods that involve cancer cells which are modified so that they can form orthotopic tumors in a non-human mammal, and wherein metastasis of the tumor can be controlled. The cancer cells, which may be human cancer cells, are modified so that expression of a human chemokine receptor can be modulated. Modulating expression of the human chemokine receptor allows selective initiation of metastasis. Kits which contain the modified cancer cells are provided. A method for identifying agents which can inhibit metastasis using non-human mammals having orthotopic tumors formed using the modified cancer cells is also included.

3 Claims, 17 Drawing Sheets

(56) References Cited

OTHER PUBLICATIONS

Yadav, V., et al., Celastrol suppresses invation of colon and pancreatic cancer cells through the downregulation of expression of CXCR4 chemokine receptor, Journal of Molecular Medicine, Dec. 2010, vol. 88, No. 12, pp. 1243-1253.

Lanati, S., et al., Chemotrap-1: An Engineered Soluble Receptor That Blocks Chemokine-Induced Migration of Metastatic Cancer Cells In vivo, Cancer Research, Aug. 24, 2010, vol. 70, No. 20, pp. 8138-8148.

Schwarz, M., et al., Lymphocyte-derived cytokines induce sequential expression of monocyte- and T cell-specific chemokines in human mesangial cells, Kidney International, 1997, vol. 52, pp. 1521-1531.

Schwarz, M., et al., IFNγ induces functional chemokine receptor expression in human mesangial cells, Clinical and Experimental Immunology, 2002, vol. 128, No. 2, pp. 285-294.

Beq, S., et al., Injection of glycosylated recombinant simian IL-7 provides rapid and massive T-cell homing in hresus macaques, Blood, Apr. 7, 2009, vol. 114, No. 4, pp. 816-825.

Shields, J.D., et al., Chemokine-mediated migration of melanoma cells towards lymphatics—a mechanism contributing to metastasis, Oncogene, 2007, vol. 26, pp. 2997-3005.

* cited by examiner

Figure 13, continued
C
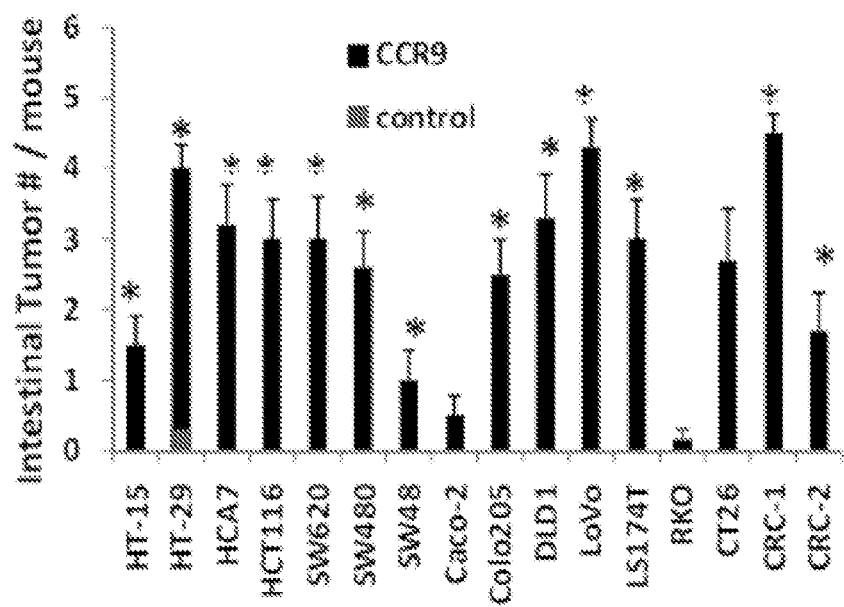

MAMMAL WITH AN ORTHOTOPIC TUMOR CAPABLE OF METASTASIS, A METHOD OF MAKING AND A METHOD OF USING

CROSS-REFERENCE TO RELATED APPLICATIONS

This application claims priority to U.S. Provisional Application No. 61/668,289, filed on Jul. 5, 2012, the disclosure of which is incorporated herein by reference.

STATEMENT REGARDING FEDERALLY SPONSORED RESEARCH

This disclosure was made with government support under grant no. R01-CA098626 awarded by the National Institutes of Health and under grant no. 1106153 awarded by the National Science Foundation. The government has certain rights in the disclosure.

FIELD OF THE DISCLOSURE

The instant disclosure generally relates to cancer and more particularly to making and using engineered human cancer cells for formation of orthtopic tumor models which can metastasize by manipulation of a chemokine axis.

BACKGROUND OF THE DISCLOSURE

Cancer remains a leading cause of death worldwide, with melanoma, ovarian, breast, prostate and colorectal cancer (CRC) being some of the most widely represented. In many cancers, metastasis is evidence of an advanced stage of cancer, and therefore a generally worse prognosis for the patient. As an example, CRC progresses through multiple distinct stages. Morphologically, inappropriate proliferation and anti-apoptosis cause formation of adenomas, which evolve into pre-invasive carcinoma in situ. Then, pre-invasive CRCs acquire the ability to invade through the submucosa and muscularis, metastasize, and survive outside the colon microenvironment niche. As 5-year survival for early stage CRC is ~90% vs. ~10% for metastatic CRC, understanding the mechanisms that regulate the transition from indolent (adenomas and carcinoma in situ) to locally invasive early clinical stage (stage I-II) and metastatic later stage (stage III/IV) CRC, as well as the stages of other metastatic cancers, is critical to improving patient outcomes. However, currently available models of cancer, such as subcutaneous xenografts which are widely used for drug screening and tumorigenicity studies do not recapitulate the tumor microenvironment of patients and seldom metastasize, which may partially explain the high rate of failure for clinical trials based on drugs identified using such models. Further, tail vein injection of cancer cells is sometimes used instead of xenografts, but this frequently does not result in optimally relevant tumor modeling. For example, tail vein injected CRC cells largely form lung tumors directly instead of gastrointestinal tumors, and while injection of CRC cells into spleen or under the kidney capsule can cause tumor formation in multiple organs, the tumors do not follow the clinical CRC metastases route. Further, it is feasible to surgically implant tumor cells to create a surgical orthotopic model, such as by implanting CRC cells into the gastrointestinal tract, but this requires highly trained technicians, is time-consuming, causes needless waste of animals who often do not survive the procedure and importantly does not robustly generate multiple liver metastasis, making such models unsuitable for drug discovery. Further still, all of these techniques require surgical procedures which create wounds and inflammation which can cause artifacts that can confound metastasis studies. Finally, while there are a number of genetically engineered animals that can form orthotopic tumors, these are typically confined to studying early events in tumorigenesis, are difficult and time consuming to make, and can have multiple significant genetic and epigenetic distinctions that make their tumors and metastatic events materially different from the human cancers they are intended to model. Thus, there is an ongoing need for improved methods, model cells and animals for use in developing improved treatments and prophylactic approaches for cancer and metastasis. The present disclosure addresses these and other needs.

BRIEF SUMMARY OF THE DISCLOSURE

In the present disclosure it is demonstrated that the Chemokine 25/Chemokine Receptor 9 (CCL25/CCR9) axis attracts injected colon cancer cells to home to the GI and inhibits colon cancer invasion and metastasis. We have harnessed this discovery to provide compositions and methods that encompass modifying cancer cells so that they can form orthotopic tumors in a non-human mammals, wherein metastasis of the tumor can be controlled. The cancer cells are modified so that expression of a chemokine receptor can be modulated. In particular, modulating expression of the chemokine receptor allows triggering metastasis from an orthotopic primary tumor. In embodiments, the cancer cells are human cancer cells. In embodiments, the chemokine receptor is a human chemokine receptor.

In one aspect, the method for making an orthotopic tumor capable of metastasizing comprises: a) introducing into a non-human mammal a plurality of cancer cells, wherein the cancer cells contain an expression vector, wherein the expression vector comprises an inducible promoter that controls expression of a chemokine receptor. In embodiments, the chemokine receptor is the CCR9 receptor. In embodiments, the chemokine receptor is the human CCR9 receptor.

In one approach, the cancer cells are CCR9+ cancer cells and they are modified to comprise an expression vector having an inducible promoter that can drive expression of a polynucleotide that can facilitate RNAi-mediated translation inhibition or degradation of human chemokine CCR9 receptor mRNA. For these cells, the orthotopic tumor forms after the cells are introduced into the non-human mammal, after which expression of the polynucleotide, such as an shRNA or an RNA oligonucleotide, is induced. This suppression of CCR9 expression is followed by metastasis of the orthotopic primary tumor.

In another approach, the cancer cells are CCR9– cells which are modified to comprise an expression vector having an inducible promoter that can drive expression of the CCR9 receptor. For the modified CCR9– cells, the orthotopic tumor forms after the cells are introduced into the non-human mammal and expression of CCR9 is induced. CCR9 expression can also be induced prior to introducing the cells into the non-human mammal, so long as the induced CCR9 expression is maintained long enough after introduction so that the primary orthotopic tumor is formed. After formation of the orthotopic primary tumor, the induced expression of the CCR9 receptor can be stopped, which results in metastasis of the primary orthotopic tumor.

Kits which contain expression vectors for making the modified cancer cells are provided, along with packaging or other printed material which describes how to use the make and use the cancer cells to form an orthotopic tumor, and optionally to trigger metastasis. The kits can in embodiments contain cancer cells which comprise the expression vectors.

A method for identifying agents which can inhibit metastasis using non-human mammals having orthotopic tumors formed using the modified cancer cells is also provided. This method comprises introducing modified cancer cells into a non-human mammal and forming an orthotopic tumor, triggering metastasis, and determining whether or not a test agent administered to the mammal inhibits the metastasis.

In this disclosure, we demonstrate that CCR9 protein expression levels are highest in colon adenomas, and progressively decrease in invasive and metastatic CRCs. It is also shown that CCR9 is expressed in both primary tumor cell cultures and colon cancer initiating cell lines (CCIC) derived from early stage (I/II) CRCs. In vivo, systemically injected CCR9+ early stage CCIC unexpectedly and spontaneously form orthotopic gastrointestinal xenograft tumors. Blocking CCR9 signaling inhibits CRC tumor formation in the native gastrointestinal CCL25+ microenvironment, while increasing extra-intestinal tumor multiplicity. These data provide insights into the mechanisms that regulate cancer progression, invasion and metastasis and provide novel in vitro and in vivo compositions, methods and compositions for use in studying tumor formation and metastasis.

DESCRIPTION OF THE DRAWINGS

In FIG. 6B, left panel, the order of bars for each sample listed on the X-axis is from left to right: Scr, CCR9 KD, Snail KD, and CD26 KD. (C) Kaplan-Meier survival analysis of mice after tail vein injection with anti-Ccl25 antibodies or CCIC lentivirally infected with scrambled shRNA control (Mock), shRNA against CCR9, SNAIL1 or CD26. Survival curve data match Table 1. P=0.0007, Log Rank test comparison of overall survival of mice injected with CCIC expressing either scrambled shRNA control vector or anti-CCR9 knockdown sequences (Graphpad Prism version 5). P=0.023 Log Rank test comparison of overall survival of mice injected with anti-Ccl25 or IgG control (Graphpad Prism version 5).

DETAILED DESCRIPTION OF THE DISCLOSURE

Figure 1:
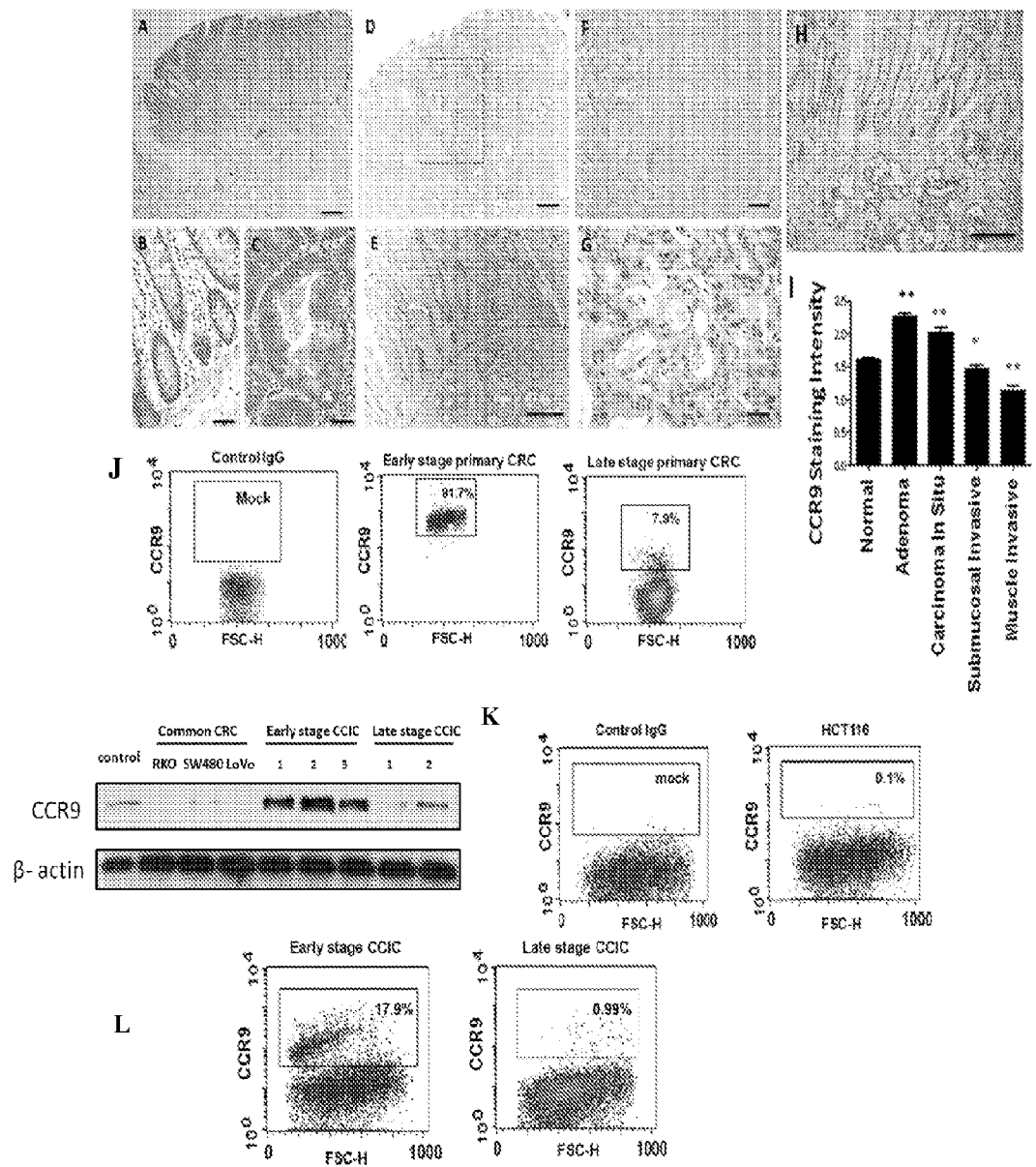
FIG. 1. CCR9 is expressed in early stage CRC and early stage colon cancer initiating cells (CCIC). CCR9 protein in normal colon epithelium (B), pre-invasive (A&C), invasive (D&E) and liver metastatic (F&G) CRCs are shown by immunohistochemistry with anti-human CCR9 and developed by DAB (brown). Dotted line in E indicates the boundary between normal epithelium (CCR9+) and invasive CRC (CCR9−). (H), negative control with control IgG; Scale bars, 100μ in A,D,F; 50μ in E,G,H; 10μ in B,C (I) CCR9 expression levels by immunohistochemistry scoring. Error bars indicate SEM. * and ** indicate statistical difference with P<0.001 and P<0.01, respectively, compared to normal colon. (J) FACS quantification of membrane and cytoplasmic CCR9+ cells in early or late stage primary CRCs. Gates are set for high CCR9+ signal intensity. (K) Western blot of CCR9 protein levels in common CRC lines (RKO, SW480, LoVo), 3 early stage CCIC lines (Stage I/II) and 2 late stage CCIC lines (Stage III/IV), β-actin is loading control. Lymphoma cells are used as a positive control for CCR9. (L) FACS quantification of cell surface membrane CCR9+ cells in common CRC lines (HCT116 as representative), early stage CCIC and late stage CCIC (early stage CCIC1 and late stage CCIC1 as representative).

The present disclosure provides compositions and methods which comprise in various embodiments cancer cells which have been modified so that expression of a chemokine receptor can be modulated. The modified cells are useful for, among other purposes, forming orthotopic tumors in non-human animals, controlling initiation of metastasis of the orthotopic tumors, and for determining whether or not test agents are capable of inhibiting metastasis. In embodiments, methods for making an orthotopic tumor capable of metastasis are provided. Also provided are kits comprising engineered cancer cells which are capable of forming orthotopic tumors.

"Orthotopic" as used herein means occurring at the expected place in the body. As a non-limiting example, in humans, colon cancer cells normally form primary tumors in the gastrointestinal tract. Thus, a primary orthotopic colon cancer tumor should form in the gastrointestinal tract of an animal model of colon cancer, but for a variety of reasons, such models have been previously difficult and costly to develop, and to the extent they have been possible at all, they require surgical implantation of cancer cells. The present disclosure has advantages over previously available techniques because it enables formation of orthotopic tumors in non-human animals using cancer cells, including human cancer cells, which are modified to permit control of metastasis from the primary tumor by modulating expression of a chemokine receptor. In embodiments, control of metastasis comprises controlling the initiation of metastasis. Thus, the present disclosure includes in various aspects cancer cells which have been engineered so that expression of a chemokine receptor can be modulated, wherein the human cancer cells have the capability to metastasize from a primary tumor based at least in part on modulation of the expression of the chemokine receptor. Additionally, orthotopic tumors of the present disclosure can be formed, for example, in a rodent without the need for surgical procedures by administration of the cancer cells via the tail vein, providing a unexpected and heretofore unavailable approach for creating orthotopic tumors and controlling metastasis of them. In embodiments, the cancer cells used in the present disclosure are human cancer cells, but cancer cells from other mammalian species can also be used, such as rodent cancer cells, including but not necessarily limited to murine cancer cells The engineered cancer cells that are an aspect of the present disclosure can be any type of cancer cells that can form a primary tumor and thereafter metastasize, subject to the capability to control metastasis that is further described herein. Likewise, the chemokine receptor, the expression of which can be modulated according to the present disclosure, can be any chemokine receptor that is involved in metastasis, and can be specific for any chemokine. Those skilled in the art will recognize that chemokines are a family of secreted ligands that play roles in regulating lymphocyte intra- and intercellular signaling, anti-apoptosis and trafficking between different organs, such as bone marrow and intestinal mucosa.

In embodiments, metastasis from the primary tumor facilitated by the present disclosure comprises metastasis to the expected location in the body of the non-human mammal, meaning that the type of orthtopic tumor metastasizes to the same organs or other locations in the non-human mammal as for the same type of tumor in a human patient. For example, human colon cancer tumors often metastasize to the lungs and liver. Thus, in non-limiting embodiments, an orthotopic primary tumor comprising engineered human colon cancer cells of the present invention also metastasizes to the lungs and liver of the non-human mammal in which the orthotopic primary tumor is formed.

In an embodiment, the chemokine receptor engineered to have controllable expression according to the disclosure is the CCR9 chemokine receptor; its ligand is the chemokine referred to as CCL25. In the present disclosure, a novel role for CCR9 in the inhibition of colorectal cancer invasion and metastasis is revealed. Without intending to be constrained by any particular theory, it is considered that the G-protein coupled chemokine receptor CCR9 and its ligand CCL25 comprise a signaling axis that is particularly relevant in the small intestine and colon. Small intestine and colon epithelial cells produce CCL25. This attracts circulating CCR9+ T cells to intravasate into the gut towards the CCL25 source. In addition to producing CCL25, endogenous small intestine and colon epithelial cells also express CCR9. However, as will be apparent from data and description presented below, we have now discovered that commonly used colorectal cancer cell lines do not express CCR9 as determined by immunohistochemistry (CCR9– cells), whereas newly derived cell cultures from primary colorectal cancer cell cultures and colon cancer initiating cell lines (CCIC) made from early stage tumors do express CCR9 (CCR9+ cells). Furthermore, melanoma, ovarian, breast and prostate adenocarcinomas express CCR9. Thus, it is apparent that CCL25/CCR9 plays a variety of roles in different cell types, including several distinct types of cancers. Accordingly, the present disclosure is expected to be applicable to a variety of cancer cell types for which modulation of chemokine receptor such as CCR9 can affect metastasis from a primary tumor. In embodiments, the engineered cells provided by the present disclosure are human CRCs which comprise one or more expression vectors which can modulate CCR9 expression as described further below.

With respect to CCR9, we demonstrate that compared to normal colon mucosa, CCR9 is upregulated in adenomas and pre-invasive colorectal cancers. In contrast, CCR9 expression is subsequently downregulated in invasive and metastatic CRCs. Because we discovered as described further herein that commonly used colorectal cancer cell lines are frequently CCR9–, new cell culture models were created and tested. We showed that both primary colorectal cancer cell cultures and CCIC lines made from early stage tumors can be CCR9+. We further demonstrate in vivo that CCR9+ early stage CCIC introduced into non-human animals spontaneously form orthotopic colon and small intestinal xenografts, which to our knowledge has never been observed with any previous CRC cell line, while commonly used, non-engineered colorectal cancer cell lines and CCR9– CCIC form only extra-intestinal tumors. We demonstrate that blocking the CCR9-CCL25 axis inhibits CCIC intestine/colon tumor formation while increasing extra-intestinal tumor multiplicity. Overall, these data provide insights into the mechanism by which CCR9/CCL25 promotes colon-localized, early stage colorectal cancer growth while inhibiting invasion and metastasis, and further demonstrate a variety of uses for the presently provided novel engineered cells and the in vivo model system we used to control CRC tumor progression and metastasis in the native colon microenvironment. We have also demonstrated using oxaiplatin treatment that metastatic tumors made according to the present disclosure are more chemoresistant than primary GI tumors and subcutaneous xenografts.

Modifying cancer cells such that expression of the chemokine receptor is controllable can be performed using different approaches that comprise either inducing expression of CCR9, or suppressing its expression. Each approach takes advantage at least in part of the present demonstration that in vitro cultures of colon cancer cells may or may not express CCR9. One approach comprises modifying CCR9+ human cancer cells such that expression of CCR9 can be suppressed. Such CCR9+ cells are considered to endogenously or constitutively express CCR9. An alternative approach comprises modifying colon CCR9– cancer cells such that expression of CCR9 can be induced. CCR9– cells are considered to be endogenously CCR9–, meaning they are CCR9– prior to being modified according to the present disclosure. CCR9– cells can be cells which do not express detectable CCR9, such as by using an immunoassay, i.e., a Western blot or an ELISA assay, or cells that express less CCR9 than a reference, such as the amount of CCR9 expressed by a colorectal cancer cell in a gastrointestinal tumor that is not metastasizing. Thus, cells which do not express CCR9 (CCR9–) cells can include cells that express lower amounts of CCR9 than a reference. In either case, when human cancer cells in the primary tumor stop expressing CCR9, either by eliminating the induced expression of CCR9 or by inducing suppression of CCR9, metastasis is triggered.

With respect to modifying CCR9+ cancer cells such that expression of CCR9 can be suppressed, in various embodiments, the method comprises introducing into the CCR9+ cancer cells an expression vector which allows inducible expression of a polynucleotide that can effect RNAi-mediated degradation of mRNA encoding CCR9. By using this approach, expression of the receptor can be controlled such that it is turned off when desired by inducing expression of the polynucleotide that can facilitate the RNAi-mediated degradation of the receptor. In embodiments, the polynucleotide that can effect RNAi-mediated degradation of mRNA encoding the CCR9 receptor is a polynucleotide that is complementary to CCR9 encoding mRNA. The polynucleotides that facilitate RNAi-mediated suppression of CCR9 expression can be in the form of shRNAs that are designed to target CCR9 mRNA. As is known in the art, shRNAs adopt a typical hairpin secondary structure that contains a paired sense and antisense portion, and a short loop sequence between the paired sense and antisense portions. shRNA is delivered to the cytoplasm where it is processed by dicer into siRNAs. The siRNAs are recognized by RNA-induced silencing complex (RISC), and once incorporated into RISC, siRNAs facilitate cleavage and degradation of targeted mRNA. In embodiments, an shRNA polynucleotide used to suppress CCR9 expression can comprise or consist of between 45-100 nucleotides, inclusive, and including all integers between 45 and 100. The portion of the shRNA that is complementary to the CCR9 mRNA can be from 21-29 nucleotides, inclusive, and including all integers between 21 and 29. shRNAs expressed from modified viruses and targeted to many human mRNAs are also commercially available.

In various embodiments, an shRNA can be present in a lentiviral vector, suitable constructs of which are known in the art and which are commercially available to be adapted for use with the presently provided compositions and methods. In embodiments, the lentiviral vector or any other suitable expression vector includes an inducible promoter that drives transcription of the polynucleotide that effects RNAi-mediated degradation of the CCR9 receptor mRNA. In general, the inducible promoter is configured such that it is operably linked to the sequence encoding the polynucleotide targeted to the CCR9 mRNA. In one embodiment, the inducible promoter is induced by an agent that is delivered to the cells and/or to the non-human animal. In embodiments, the promoter can be induced by an antibiotic, for example the promoter can be a doxycycline-inducible promoter. A schematic representation of an expression vector comprising a doxycycline-inducible promoter controlling expression of an shRNA targeted to CCR9 mRNA is presented in FIG. 7A. Those skilled in the art will recognize that there are a wide variety of well-known methods and techniques for introducing polynucleotides, including expression vectors/letiviral vectors, into cancer cells, and any such techniques can be used for making the engineered human cancer cells of the present disclosure.

In embodiments, the disclosure includes in vitro cultures of colon cancer cells comprising an expression vector comprising an inducible promoter that can drive transcription of an shRNA targeted to CCR9 mRNA. In embodiments, the disclosure includes an orthotopic tumor comprising colon cancer cells comprising an expression vector which contains an inducible promoter that can drive transcription of an shRNA targeted to CCR9 mRNA. In embodiments, the invention includes a non-human animal comprising metastatic foci, wherein the metastatic foci comprise human cancer cells which contain an expression vector comprising an inducible promoter that can drive transcription of an shRNA targeted to CCR9 mRNA. In embodiments, the metastatic foci comprise colon cancer cells comprising the expression vector which contains the inducible promoter that can drive transcription of an shRNA targeted to CCR9 mRNA, wherein the transcription of the shRNA is induced and therefore expression of CCR9 receptor is inhibited.

Figure 12:
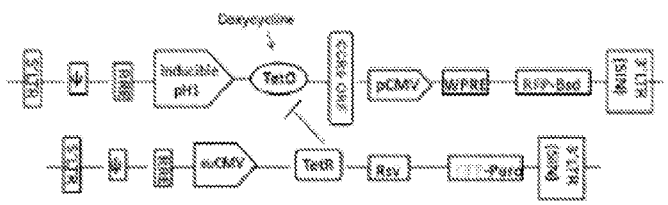
FIG. 12. (A) Graphical representation of CCR9 inducible expression vector. (B) Western blot validating induction of CCR9 expression. (C) Graphical data demonstrating that CCR9 overexpression does not significantly affect cell growth and viability. (D) Boyden chamber experiment results summarized graphically and showing that the indicated cells with induced CCR9 expression functionally migrate to CCL25.
Figure 12:
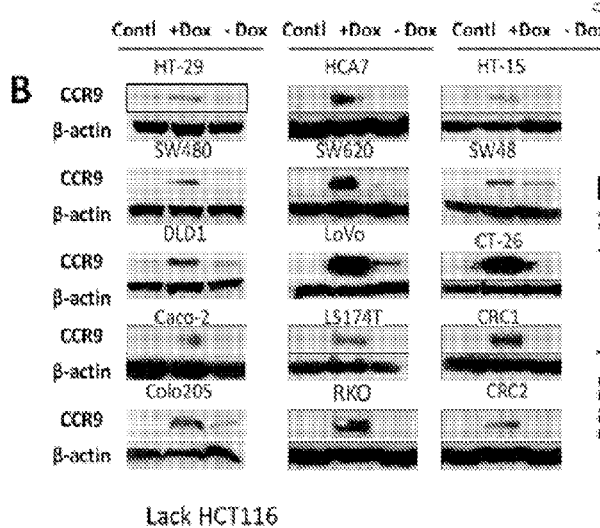
Figure 12:
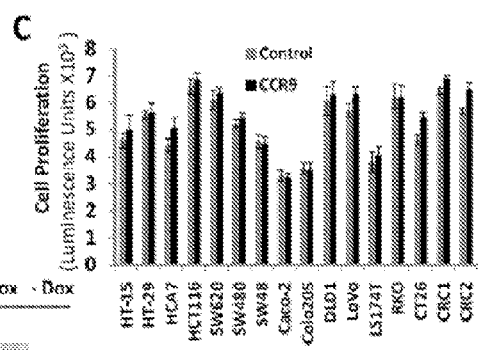
Figure 12:
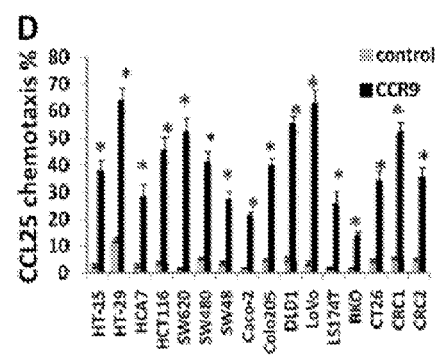
Figure 13:
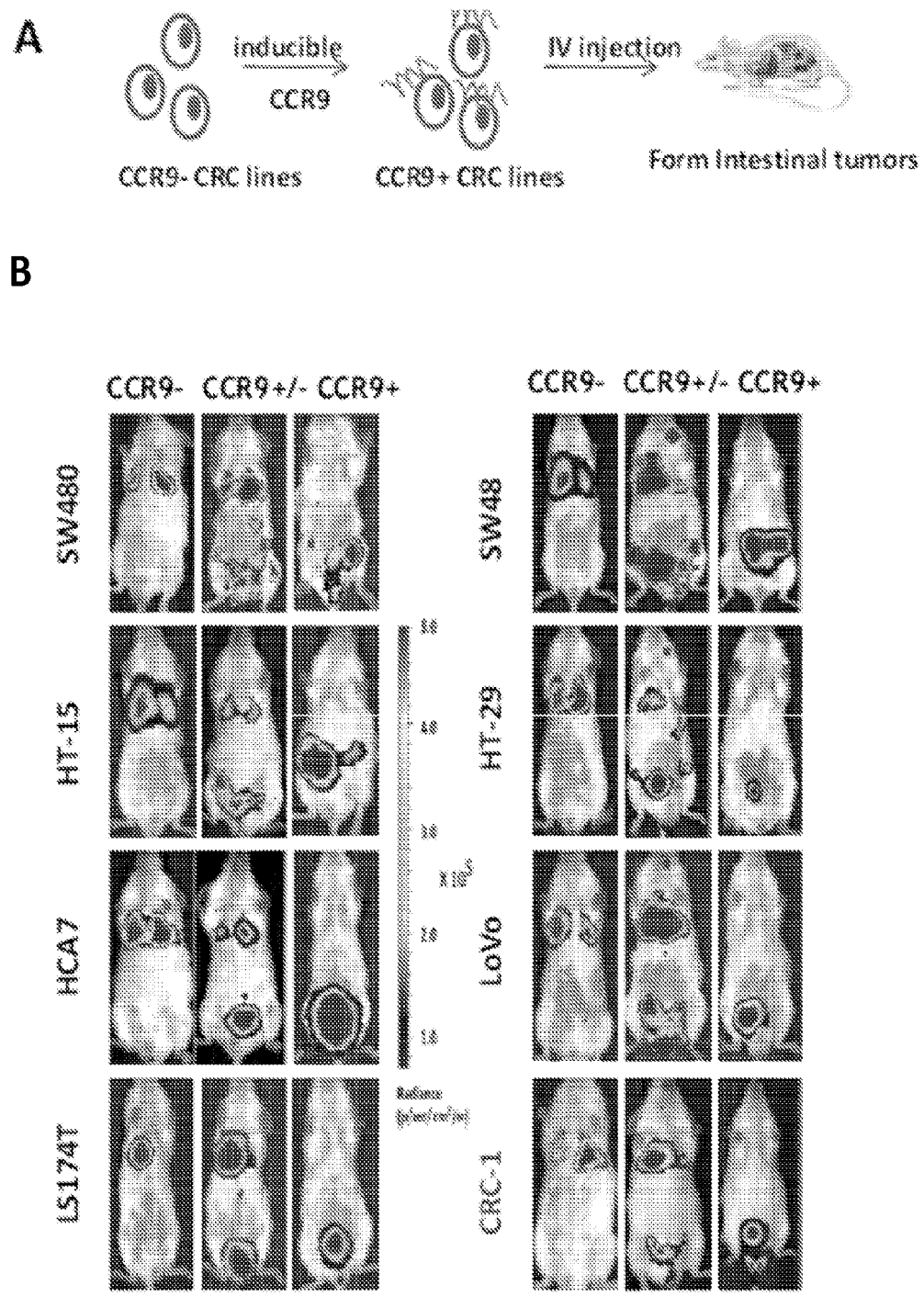
FIG. 13. (A) Schematic showing cancer cells with induced CCR9 expression injected via tail vein form gastrointestinal tumors. (B) Whole body imaging showing 12 human CRC lines with induced CCR9 expression developed gastrointestinal tumors in immunodeficient mice. (C) Graphical summary of results showing intestinal tumor formation using the different cell lines indicated with induced CCR9 expression. Two primary lines and lines derived from patients formed GI tumors.
Figure 14:
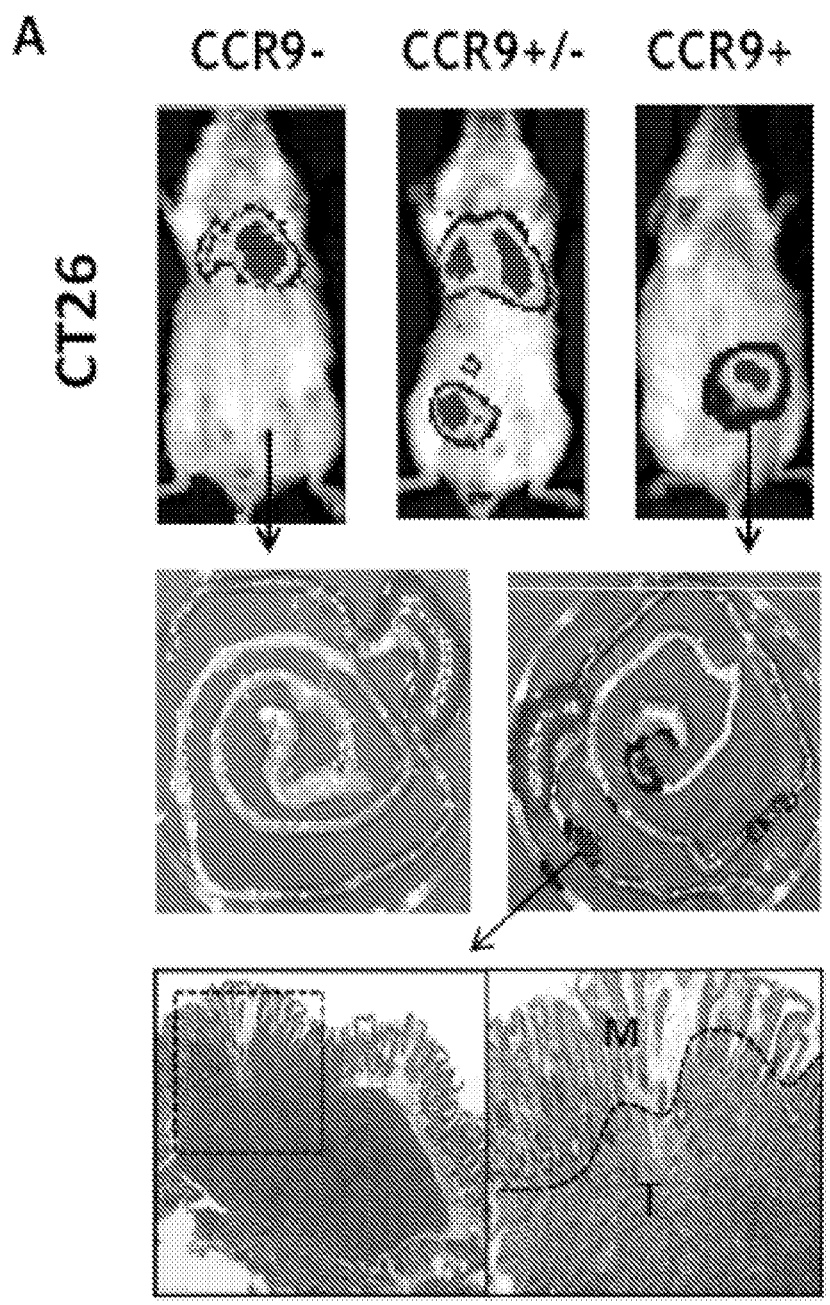
FIG. 14. Photographic/imaging representations showing that CT26 cells with induced CCR9 expression form GI tumors in immunoproficient mice.
Figure 15:
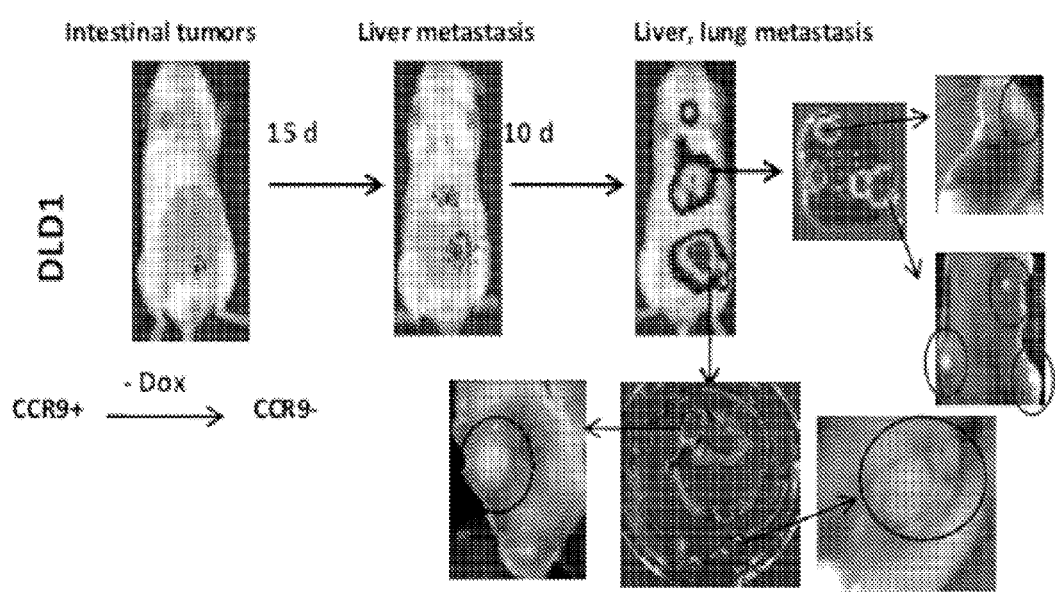
FIG. 15. Imaging representations of showing formation of orthotopic intestinal tumors followed by cessation of CCR9 induction (−Dox) followed by liver and lung metastasis. We followed similar models to demonstrate the dynamics of CRC metastasis progression by real time IVIS imaging and the interaction with vasculature, such as intravasation of GI tumors and extravasion of liver tumors by multiple photon microscopy (not shown).

With respect to modifying CCR9− cancer cells such that expression of CCR9 can be induced, in various embodiments, the method comprises introducing into the CCR9− cancer cells an expression vector which allows inducible expression of a polynucleotide that encodes CCR9. In general, the inducible promoter is configured such that it is operably linked to the CCR9 coding sequence. An illustrative example of an expression vector comprising an inducible promoter that drives transcription of a CCR9 mRNA coding sequence is presented in FIG. 12A. In an embodiment, the CCR9 that is induced or that is inhibited comprises or consists of the sequence of SEQ ID NO:1. SEQ ID NO:1 is: MTPTDFTSPIPNMADDYGSESTSSMEDYVNFN-FTDFYCEKNNVRQFASHFLPPLYWL VFIVGAL-GNSLVILVYWYCTRVKTMTDMFLLNLAIADLL-FLVTLPFWAIAAADQWK FQTFMCKVVNSMYKMN-FYSCVLLIMCISVDRYIAIAQAMRAHTWREKRLLY-SKMV CFTIWVLAAALCIPEILYSQIKEESGIAICTMVYPS-DESTKLKSAVLTLKVILGFFLPFV VMACCYTII-IHTLIQAKKSSKHKALKVTITVLTVFVLSQFPYNCILL-VQTIDAYAMFIS NCAVSTNIDICFQVTQTIAFFHSCLNPVLYVFVGER-FRRDLVKTLKNLGCISQAQWVS FTRREGSLKLSSML-LETTSGALSL (SEQ ID NO:1). This is the sequence of Variant A CCR9 and is the deduced amino acid sequence from the cDNA sequence provided in GenBank accession no. NM_031200. The 16 C-terminal amino acids shown for SEQ ID NO:1 (KLSSMLLETTSGALS; SEQ ID NO:2) are optional; truncating them results in CCR9 Variant B. It is expected that Variant A or B can be used for the purposes of this disclosure. Those skilled in the art will recognize that various amino acid substitutions to the Variant A or B amino acid sequence can be made, such as conservative amino acid substitutions, or additions or deletions, so long as the CCR9 polypeptide retains its ligand binding function and CCR9+ cells are capable of forming orthotopic tumors as described herein. It will also be recognized by those skilled in the art that any expression vector encoding an mRNA which encodes a CCR9, such as Variant A or Variant B CCR9 mRNA can be used in the compositions and methods provided by the instant disclosure. Likewise, any RNA for use in RNAi-mediated suppression of CCR9 can target any mRNA that encodes either Variant. In embodiments, Variant A is used. In this regard, we have determined that Variant A shows higher affinity to CCL25 in CRC cells. In one embodiment, a cDNA encoding Variant A comprises SEQ ID NO:3, or a segment thereof that comprises an open reading frame that encodes Variant A or Variant B CCR9. In an embodiment, Variant A is encoded by nucleotides 181-1290 of SEQ ID NO:3, having a total length of 1110 bp. In an embodiment, Variant B is encoded by nucleotides 168-1241 of SEQ ID NO:3. The RNA equivalent of SEQ ID NO:3 is encompassed by this disclosure.

We used the inducible expression vector in the human CRC lines SW480, SW620, SW48, HCT116, HCT15, LoVo, Caco2, HT-29, Colo205, RKO, DLD1, LS174T, HCA7, in mouse CRC lines Colo26, CT26, and in primary CRC lines J212, J217, J906, J1108, S 1024. The capability of CCR9 induced expression from CRC cells engineered for the capability to form orthotopic tumors which metastasize subsequent to cessation of CCR9 induction is demonstrated collectively by the data presented in FIGS. 12, 13, 14 and 15.

In embodiments, the disclosure includes in vitro cultures of colon cancer cells comprising an expression vector comprising an inducible promoter that can drive transcription of CCR9 mRNA. In embodiments, the disclosure includes an orthotopic tumor comprising colon cancer cells comprising an expression vector which contains an inducible promoter that can drive transcription of CCR9 mRNA. In embodiments, the expression of CCR9 in the cancer cells in the tumor is induced. In embodiments, the invention includes a non-human animal comprising metastatic foci, wherein the metastatic foci comprise human cancer cells which contain an expression vector comprising an inducible promoter that can drive transcription of CCR9 mRNA. In embodiments, expression of the CCR9 mRNA in metastatic foci is not induced.

In embodiments, the agent that induces transcription (the "inducer") from the inducible promoter in the engineered cancer cells is supplied by way of introducing it into a cell culture comprising the cancer cells, or by introducing it into a non-human animal into which the engineered cells have also been introduced. The inducer can be delivered in vitro or to the non-human animal using any suitable technique, such as by contacting an in vitro cell culture comprising the engineered cancer cells with the inducer, or by administering the inducer to the non-human animal by intravenous administration, or by including the inducer in substances consumed by the non-human animal, including but not necessarily limited to pharmaceutical preparations that comprise the inducer, and food and/or water that contain the inducer and which are consumed by the non-human animal.

In general the inducer is administered experimentally, and is thus not an inducer that is produced by the cell in which the expression vector is introduced, and/or it is not an inducer that is made by a cell in proximity to the engineered cancer cell, and/or it is not produced by a the non-human animal into which the cells have been introduced. Inducers of the invention in embodiments can exclude certain agents that can function to induce expression of a chemokine receptor, including but not necessarily limited to interleukins, lipopolysaccharides, antibodies, polynucleotides and immunomodulatory compositions, such as components of major histocompatibility (MHC) complexes or immunogenic polypeptides.

It will be apparent from the foregoing that one aspect of the invention comprises a method for making an orthotopic tumor capable of metastasizing, the method comprising: a) introducing into a non-human mammal a plurality of cancer cells, which may be human cancer cells, wherein the cancer cells contain an expression vector, wherein the expression vector comprises an inducible promoter that controls expression of: i) an shRNA targeted to a chemokine CCR9 receptor mRNA, which may be a human chemokine CCR9 receptor mRNA, wherein the human cancer cells are CCR9+ cells; or ii) the chemokine CCR9 receptor, wherein the cancer cells are CCR9– cells, which may be human cancer cells. In the case of i), the metastasis can occur subsequent to inducing expression of the shRNA. In the case of ii), metastasis can occur subsequent to allowing induced expression of the CCR9 to stop. In embodiments, the orthotopic tumor forms in the gastrointestinal tract of the non-human animal. In embodiments, metastasis of the gastrointestinal tumor is to the liver, lung, or peritoneum of the non-human animal. Non-human animals made according to the foregoing methods are also provided by the invention. In embodiments, the non-human animals are mammals, such as rodents. In embodiments, the rodents are mice.

In another aspect, the present disclosure provides a method for determining whether one or more test agents are candidates for use as metastasis inhibitors in humans. The method comprises providing a non-human animal model made according to the present disclosure, wherein the non-human animal has an orthotopic tumor comprising colon cancer cells as described herein, and allowing metastasis by either inducing expression of an shRNA targeted to CCR9 in endogenously CCR9+ cancer cells in the orthotopic tumor, or by stopping the induced expression of CCR9 in endogenously CCR9– cancer cells in the orthotopic tumor, and administering a test agent to the non-human animal. A reduction in metastasis relative to a control is indicative that the test agent is a candidate for use as a metastasis inhibitor in humans. In embodiments, the orthotopic tumor forms in the gastrointestinal tract of the non-human animal. In embodiments, metastasis of the tumor to liver, lung, or peritoneum of the non-human mammal is inhibited by the test agent. It will be recognized that test agents that do not inhibit metastasis in the non-human animal may be considered to be less desirable candidates for inhibition of metastasis in humans, or not candidates for such a purpose.

The control for testing of the test agents can be any suitable control. In embodiments, the control is a non-human animal of the same species as to which the test agent is administered, but in which the shRNA is not induced for CCR9+ human cells, or in which CCR9 receptor expression is not induced for CCR9– human cancer cells, as appropriate for the experimental animal(s). Those skilled in the art will also recognize that control animals can include those in which empty expression vectors are administered, but to which the inducing agent is also administered, as appropriate. In an embodiment, a test agent identified as a candidate for use as an inhibitor metastasis according to the disclosure is a candidate for use in inhibiting metastasis of a colon cancer tumor in a human subject.

In another aspect the present disclosure provides a product for use in making an orthotopic tumor capable of controllable metastasis as described herein. The product comprises at least one sealed, sterile container comprising one or more expression vectors wherein the expression vector comprises an inducible promoter that controls expression of: i) an shRNA targeted to a human chemokine CCR9 receptor mRNA for use with CCCR9+ cancer cells; or ii) the human chemokine CCR9 receptor for use with CCR9– cancer cells. The container can be any suitable container for holding expression vectors. In embodiments, the kits can further comprise CCR9+ and/or CCR9– cancer cells, including but not necessarily limited to human cancer cells, such as human colon cancer cells. The cells can comprise the expression vectors, or the cancer cells can be provided in separate, sterile sealed containers apart from the expression vectors and their respective container(s). The cells can be provided as a cooled or frozen composition, such as a suspension. The composition comprising the cells can include a component to inhibit the formation of ice crystals, such as glycerol. The product further comprises printed material providing instructions for introducing the expression vectors into cancer cells, and can also include instructions for inducing expression from the inducible promoter. The kits can also include instructions for introducing the cancer cells comprising the expression vector into a non-human mammal. The instructions can also include information regarding inducing expression of the human chemokine receptor or the shRNA, and information regarding inducing expression so that an orthotopic tumor comprising the human cancer cells forms and/or metastasizes in the non-human mammal. The product may be provided as a kit. The kit can if desired optionally include a label attached to or packaged with the container which holds the expression vectors and optionally the cells, the label describing the contents of the container and providing indications and/or instructions regarding use of the contents of the container for making engineered cancer cells and for using the cancer cells to make non-human animal models with orthotopic tumors. In embodiments, the kit further comprises the inducing agent, which can be provided in a separate container.

The following examples are presented to illustrate the present disclosure. They are not intended to limiting in any manner.

Example 1

CCR9 is upregulated in pre-invasive CRC and downregulated in invasive and metastatic CRC. To analyze the expression pattern of CCR9 in colorectal cancer, representative sections from patient tumors were immunostained. Cases varied in clinical stage from adenoma to carcinoma in situ (Tis) to transmural involvement (T4). CCR9 staining intensity was scored for normal crypt epithelium and neoplastic tissue from each involved layer of the colon wall (FIG. 1). CCR9 is expressed in normal colonocytes essentially throughout the entire crypt. To quantify CCR9 staining intensity, a histopathology scoring system ranging from 0-3 was used. Normal colon epithelium had a mean staining intensity of 1.60±0.04, n=55. CCR9 staining in adenomatous foci was significantly increased (2.26±0.06, n=46) vs. normal tissue. In contrast, staining intensity progressively decreased in carcinoma in situ (2.03±0.08, n=19), and in carcinomas invasive into the submucosa (1.47±0.06, n=44) and muscle wall (1.13±0.08, n=42; all p<0.001) (FIG. 1 A-I). Additionally, CCR9 expression in primary CRC culture by FACS were quantified. Consistently, high percentages (~90%) of early stage (I/II) primary CRC cells are CCR9+, while much lower percentages of late stage (III/IV) invasive or metastatic CRCs (~10%) are CCR9+ (FIG. 1 J). Overall, CCR9 levels are highest in non-invasive tumors (adenomas and in situ carcinomas) and progressively downregulated in submucosal invasive, muscle invasive and metastatic colorectal cancer tumors, consistent with a potential role for CCR9 to suppress invasion and metastasis.

To understand CCR9's role in colorectal cancer, several commonly used colorectal cancer cell lines were tested (HCT116, RKO, SW480 and LoVo) and found very low or undetectable CCR9 protein levels (FIG. 1 K,L). In contrast, several colon cancer initiating cell lines (CCIC) derived from early-stage/colon-localized (American Joint Committee on Cancer stage I/II) CRC patients generally have robust CCR9 protein expression. In contrast, CCIC lines derived from later stage (III/IV) patients whose tumors had spread beyond the colorectum have much lower CCR9 expression. This suggested that CCIC lines derived from early stage/colon-localized colorectal cancer patients might be a useful system for mechanistic studies of CCR9. Additionally, while only correlative, these data are consistent with immunohistochemistry that CCR9 protein levels are more closely associated with earlier stage CRC tumors that have less invasive and metastatic potential vs. later stage tumors with poorer prognosis.

Figure 2:
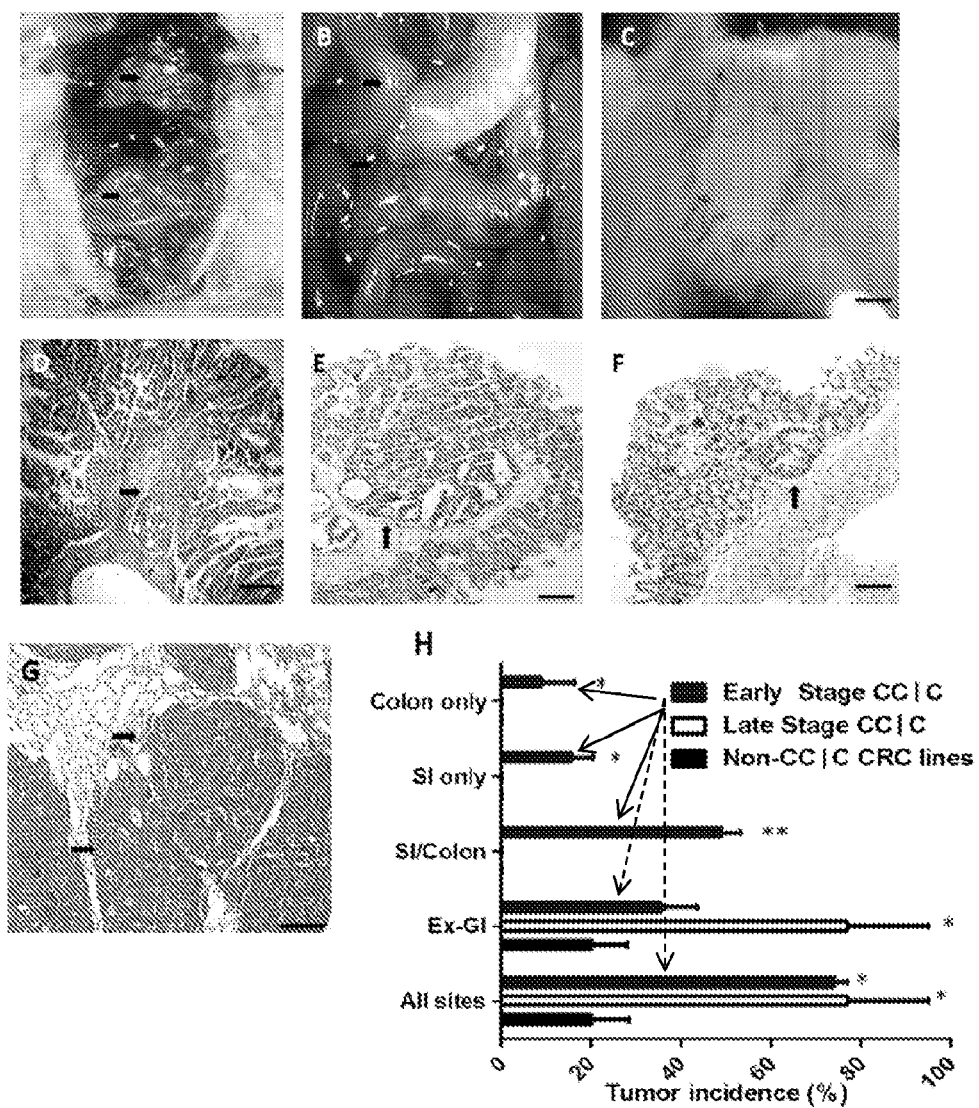
FIG. 2. Early stage CCIC form orthotopic xenograft tumors in mouse intestine, colon and other sites. (A) Postmortem analysis of NOD/SCID mice with tail vein-injected CCIC (4×). Arrows show CCIC tumors in lung (white spots; upper part of photo) and intestine (lower part of photo). Small bowel is distended and inflamed. (B) Close up of mouse abdomen showing (1) distended small intestine loop proximal to CCICtumor obstruction with adhesion to adjacent (non-obstructed and grossly normal) small intestine loop and (2) Pneumatosisintestinalis from bacterial stasis in right colon proximal to another CCIC obstruction. (C) High low power light microscopy close up of CCIC jejunal adenocarcinoma, Scale bars, 0.5 mm Multiple CCIC tumors with histopathology in small intestine (D), colon (E&F) and lung (G). Arrow denotes adenocarcinomas in D-G. Scale bars, 100μ. (H) Xenograft tumor incidence by site of implantation mice injected with CCIC or CRC cell lines. *P<0.01 and **P<0.001 compared to non-CCIC. Error bars indicate S.E.M. Arrows designate Early Stage CCSC bars.

Stage I/II CCIC form orthotopic xenograft CRC tumors in the colon and small intestine CCL25 produced by small intestine and colon epithelial cells attracts circulating CCR9+ T lymphocytes. To understand the in vivo role of CCR9 in colorectal cancer, CCIC lines were injected systemically into the tail vein of immunodeficient mice (NOG mice). 73.3% of mice injected with early stage CCIC became moribund and developed average of 3.7 tumors in intestine/colon at mean 8.55 weeks post-inoculation (Table 1). Of mice that developed gastrointestinal (GI) tumors, 69% had tumors in both small intestine and colon, 19% only in colon and 12% only in small intestine (FIG. 2 H). No upper GI or rectal tumors were seen. Many of these tumors caused intestinal obstructions and pneumatosis coli (gas in the intestine from bacterial stasis and dysmotility secondary to obstruction) (FIG. 2 A,B), pathologies often seen in patients with obstructing primary colorectal cancer adenocarcinomas. Evaluation of other organs showed that 35.6% of mice developed an average of 126 extra-intestinal tumor foci, mostly lung, and all were in mice that also carried intestine/colon tumors. In contrast, mice injected with CCIC derived from later stage tumors or commonly used colorectal cancer cell lines SW480 or LoVo formed tumors only outside the small intestine and colon (FIG. 2 H,I). Similar to CCIC dermal xenografts and the vast majority of human primary and metastatic colorectal cancer tumors, CCIC colon/intestine and extra-GI tumors have adenocarcinoma morphology containing distorted crypt-like structures (FIG. 2 D-F).

Figure 3:
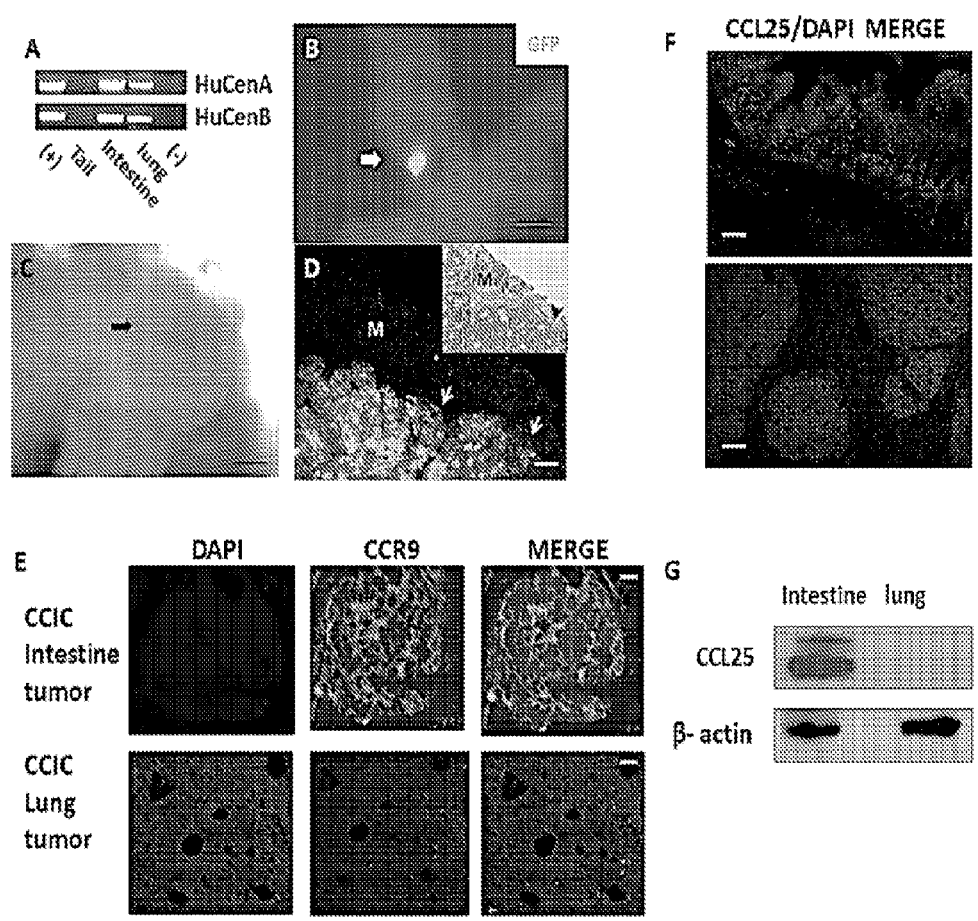
FIG. 3. CCIC colon and intestinal tumors consist of human cells and are CCR9 positive. (A). PCR of human centromeric repeat sequences from DNA extracted from CCIC (positive control), CCIC injected mouse tail, intestine, lung tissue and no DNA control (negative control). (B). Maestro GFP imaging system images of intestinal tumor of PGK-eGFP expressing CCIC. Scale bars, 0.5 cm. (C). Light microscopy close up of eGFP+ CCIC tumor in (B). Scale bars, 0.5 mm (D). Anti-GFP-immunofluorescence imaging of CCIC intestinal tumor with adenocarcinoma morphology. Left upper window shows H+E staining of the same intestinal tumor as control. Arrows indicated eGFP+ cells. M, mucosa. Scale bars, 100μ. (E). CCR9 immunofluorescence of CCIC intestinal and lung tumors. CCR9 protein was detected by anti-human CCR9 antibody (green) and nuclei were stained with DAPI (blue). Scale bars, 50μ. (F). CCL25 immunofluorescence in mouse intestine and lung. CCL25 expression was detected by anti-mouse CCL25 antibody (red) and nuclei were stained with DAPI (blue). Scale bars, 100μ. (G). Anti-Ccl25 antibody western blot showing CCL25 expression in mouse intestine but not lung. β-actin is loading control.
Figure 7:
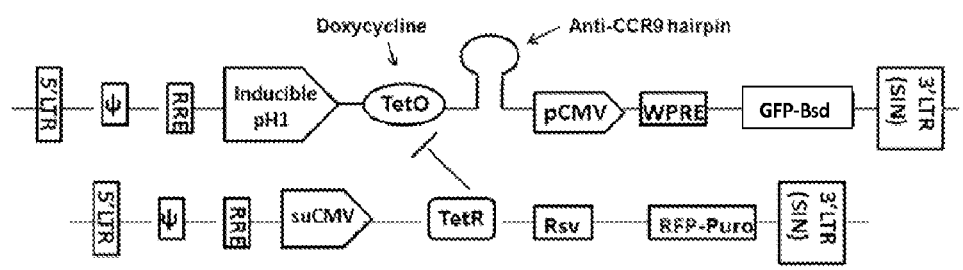
FIG. 7. CCR9/CCL25 signaling is inhibited after CCIC intestinal tumor initiation by anti-CCL25 antibody treatment or CCR9 inducible shRNA. (A). Schematic of CCR9 inducible shRNA, in which anti-CCR9 hairpin sequence was cloned in the 3'pH1 TetO promoter. Expression of anti-CCR9 hairpin was inhibited by TetR (Tet-repressor) and induced by tetrycycline derive doxycycline. (B). Efficiency of CCR9 inducible knockdown in CCIC. The CCR9 protein levels in CCICs with only shRNAtetO vector, tetO+tetR or tetO+tetR+ doxycycline were detected by anti-human CCR9 antibody (left) and semi-quantified (right) by Quantitity One (BioRad). (C & D) Xenograft tumor incidence in mice injected with CCR9+ CCR9, and anti-CCL25 antibody therapy (D) or CCR9 inducible knockdown (or control, scr) by doxycycline (E) three weeks after tail vein injection organized by tumor site. *P<0.01 compared to mock control. Error bars indicate S.E.M.
Figure 7:
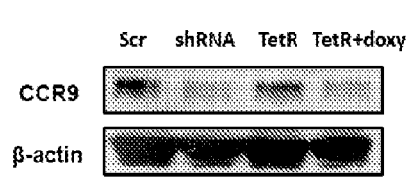
Figure 7:
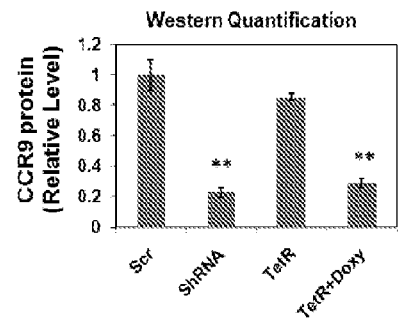
Figure 7:
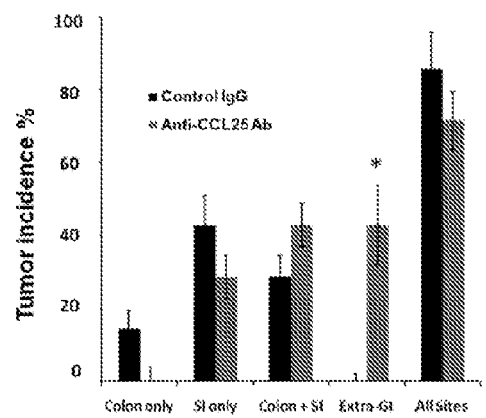
Figure 7:
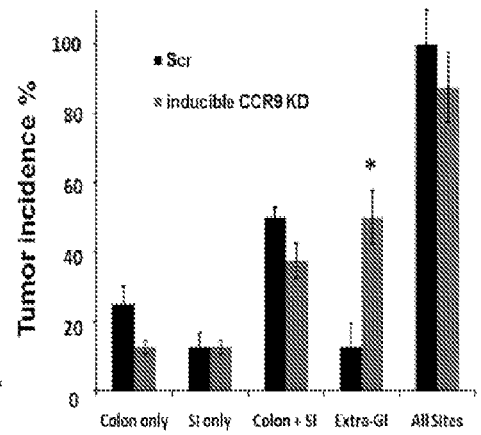
Figure 7:
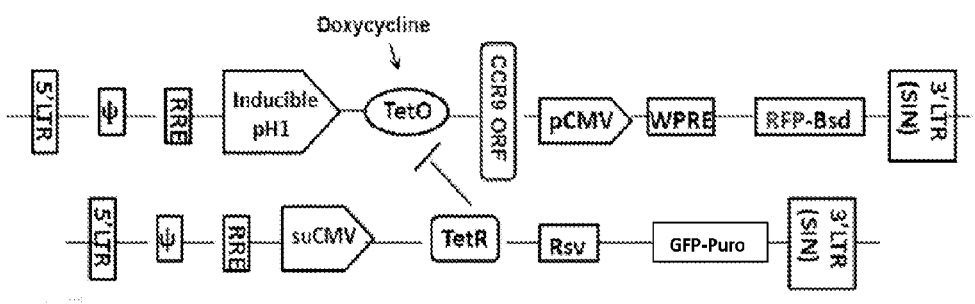

Mice injected with either early or late stage CCIC also became moribund at significantly earlier times post-inoculation vs. commonly used CRC cell lines (P<0.001) (FIG. 7). The colon/intestine tumors observed could have arisen directly from early stage CCIC, or indirectly by stimulating endogenous mouse intestinal tumorigenesis. We systemically injected and tracked early stage CCIC carrying the PGK promoter driving constitutive expression of an eGFP reporter. First, it was tested whether these tumors contained human DNA. PCR using two different human centromeric repeat sequences from genomic DNA isolated from intestine/colon tumors showed that they contain human DNA (FIG. 3 A). Next, the lower GI tract from mice carrying early stage CCIC colon/intestine tumors for eGFP fluorescence were examined. This revealed that GI tumors consist of eGFP+ cells (FIG. 3 B, C, D), indicating that the colon/intestine tumors were formed by early stage CCIC in mouse hosts. As anticipated, the intestine and colon sites where tumors formed expressed Ccl25 while sites of ex-GI tumors, such as lung, did not have detectable levels (FIG. 3F, G). Interestingly, early stage GI CCIC tumors were CCR9+ whereas ex-GI tumors were CCR9− (FIG. 3E).

Figure 4:
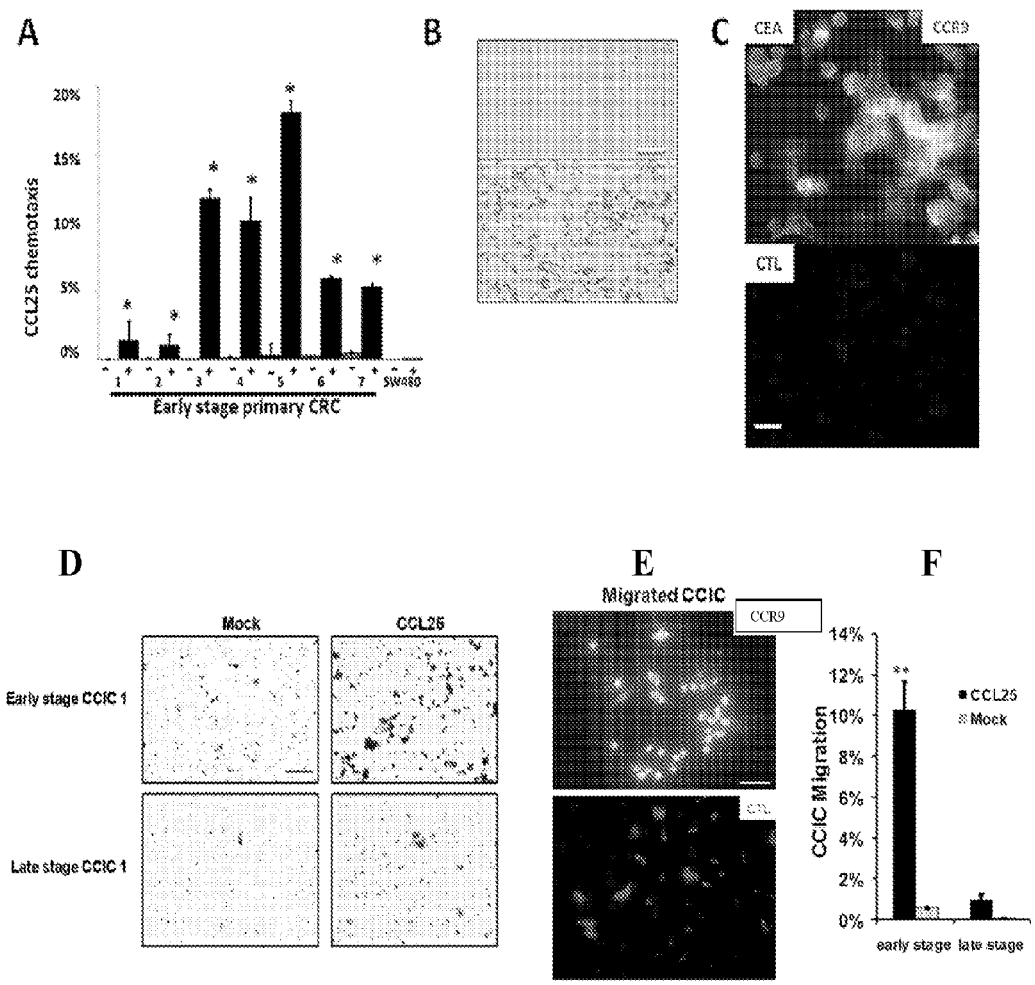
FIG. 4. CCL25 dependent chemotaxisin early stage primary CRC and CCIC. (A) Boyden chamber assay of 7 early stage primary CRCs chemotaxis to chamber containing CCL25. (−) CCL25 absence or (+) CCL25 presence. Error bars indicate S.E.M. *P<0.0001 compared to matched (−) cells by one-way ANOVA (n=4). SW480 is used as a negative control. (B) Crystal violet staining of early stage primary CRC cells migrating into chamber with CCL25 (bottom) or mock (top). Scale bar, 50μ. (C). CEA (Red) and CCR9 (green) immunofluorescence of early stage primary CRC cells that migrated to chamber with CCL25. DAPI, blue. Scale bar, 10μ. IgG is negative control. (D) Crystal violet staining of Transwell chambers with early stage CCIC1 or late stage CCIC1 (as representatives) that have migrated to CCL25 or PBS (mock). Scale bar, 50μ. (E) CCR9 immunofluorescence of early stage CCIC that migrated to CCL25 containing chamber. CCR9 (green) and DAPI (blue). Control IgG is used as negative control. Scale bar, 10μ. (F) Percentage of early or late stage CCIC that migrated to CCL25 or mock (PBS) in Transwell assay. **P<0.001.
Figure 5:
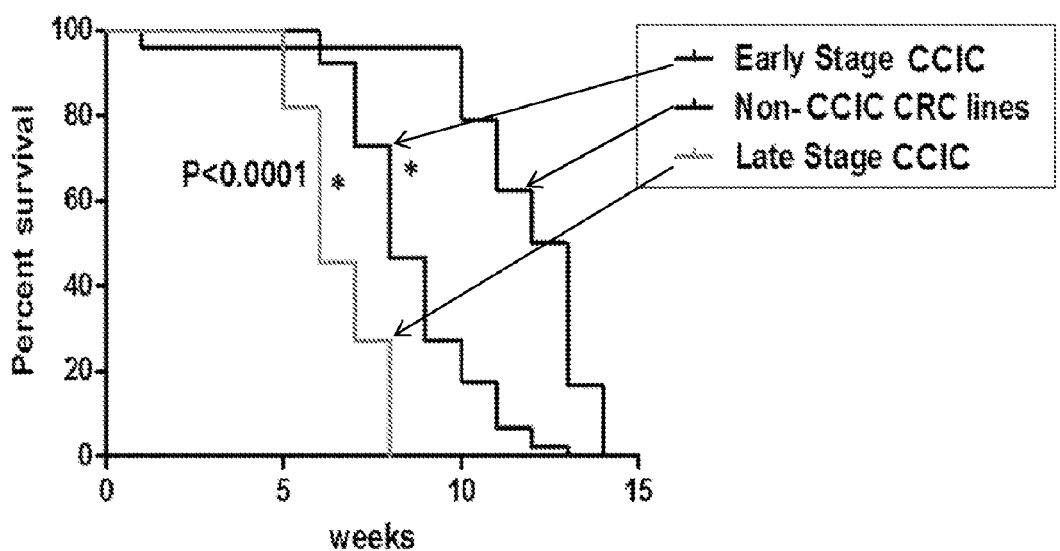
FIG. 5. Survival of mice systemically injected with early stage CCICs, late stage CCICs and non-CCIC CRC lines. Kaplan-Meier survival analysis of mice after tail vein injection with early stage CCIC (blue), late stage CCIC (grey) or the non-CCIC commonly used CRC cell lines LoVo and SW480 (black). P<0.0001 difference between the early stage CCIC and commonly used CRC cell lines by log-rank test (Graphpad Prism software version 5).

Stage I/II primary CRC cultures and CCIC show CCL25 dependent chemotaxis. To understand the role of the CCR9/CCL25 axis in primary colorectal cancer cells, tumor cells were cultured directly from patient tumors. Cells were sorted for expression of the colorectal cancer marker carcinoembryonic antigen (CEA) and plated in Boyden chambers. Consistently, more primary early stage colorectal cancer cultured cells migrated toward the chamber compartment containing recombinant CCL25 than mock control (p<0.001) (FIG. 4 A, B) while SW480 did not. Migrated primary early stage colorectal cancer cells were double immunopositive for CEA and CCR9 (FIG. 4 C). Similarly, consistent with our in vivo xenograft studies, more early stage CCIC migrated in vitro towards a chamber containing CCL25 vs. a mock control while this activity overall was much lower for experiments with late stage CCIC (FIG. 4 D-F). Altogether, these data show that both CCR9+ early stage colorectal cancer cells and CCIC functionally chemotax towards CCL25.

Figure 9:
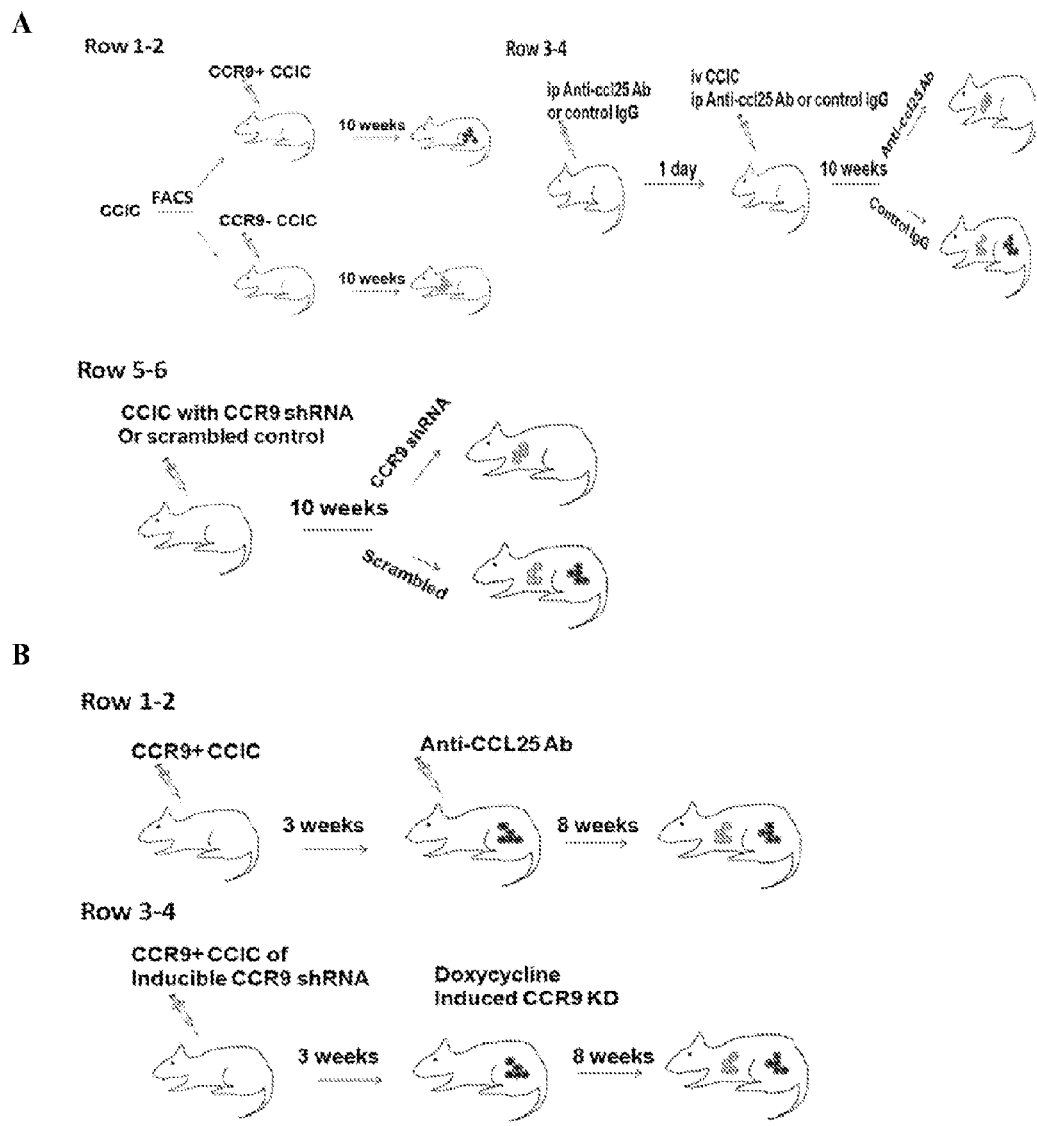
FIG. 9. (A). Schema of the experimental procedures in Table 2. (B) Schema of the experimental procedures in Table 3. Colon/intestine tumors (blue) and ex-GI tumors (green) dots.

Inhibiting the CCR9/CCL25 axis reduces CCIC colon/intestine tumor formation. To test the role of CCR9 in CCIC orthotopic colon/intestine xenograft formation, cell sorting was performed for CCR9 and systemically injected CCR9+ or CCR9− early stage CCIC (FIG. 9A). Mice injected with CCR9+ CCIC had a high incidence of colon/intestine tumors (both sites produce CCL25), whereas CCR9− CCIC had low incidence (P<0.001) (Table 2). The mean number of colon/intestine tumors in mice injected with CCR9+ CCIC was also significantly higher than mice injected with CCR9− CCIC. At the same time, the incidence and mean number of tumors outside the colon/intestine were significantly higher in mice injected with CCR9− vs. CCR9+ CCIC (Table 2).

To confirm the role of CCR9/CCL25, anti-CCL25 antibodies were used to inhibit bioavailable intestinal CCL25. Pre-treating mice with anti-CCL25 antibodies before and concurrent with early stage CCIC injection reduced colon/intestine tumor multiplicity (FIG. 9A). Anti-CCL25 antibody treatment also trended towards reduced colon/intestine tumor incidence and increased ex-GI incidence and multiplicity, although these differences were not statistically significant (Table 2). Additionally, CCR9 short hairpin RNA (shRNA) knockdown in CCIC was used. Mice injected with CCR9 shRNA knockdown CCIC had lower incidence, mean number of colon/intestine tumors and higher mean extra-intestinal tumors vs. mice injected with CCIC expressing a control shRNA (Table 2 and FIG. 6B). The overall survival of mice injected with anti-Ccl25 antibodies or CCR9 shRNA knockdown CCIC was also significantly longer vs. control (Table 2 and FIG. 6C).

Figure 8:
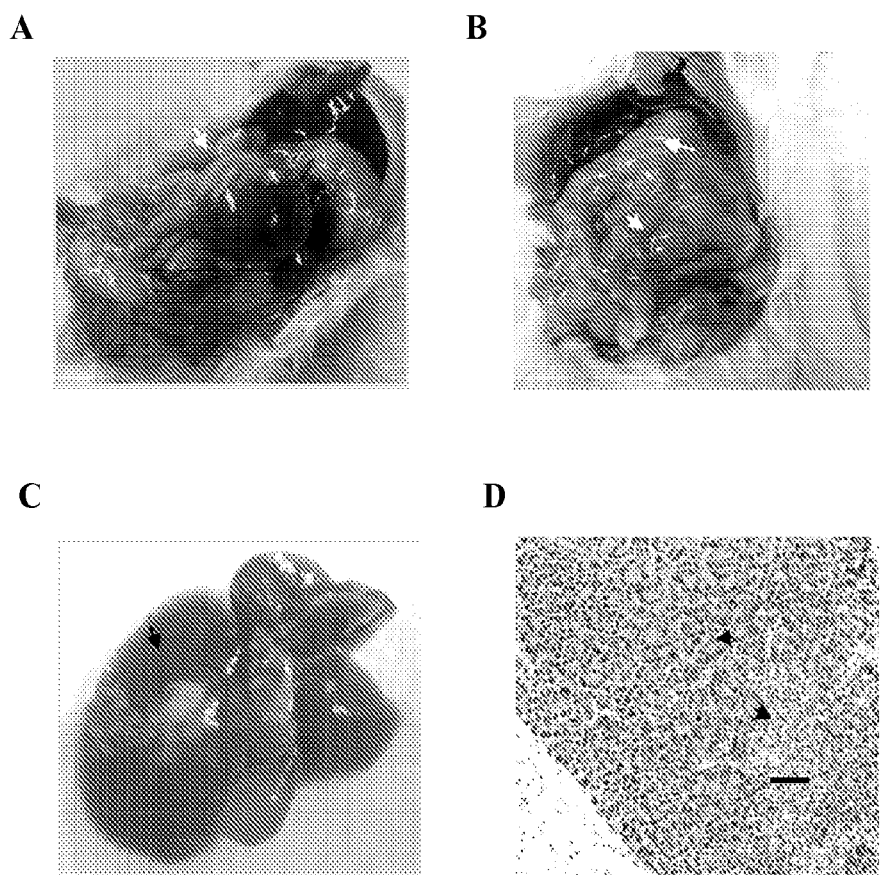
FIG. 8. CCIC extra-GI metastatic tumors are induced by anti-CCL25 treatment or CCR9 inducible knockdown. (A) and (B) Light microscopy of CCIC abdominal metastasis. (C) Light microscopy of CCIC liver metastasis, Metastatic foci are indicated by arrows. (D). H+E of CCIC metastatic tumors in pancreas. Arrows denote metastatic foci. Scale bar, 100μ.
Figure 10:
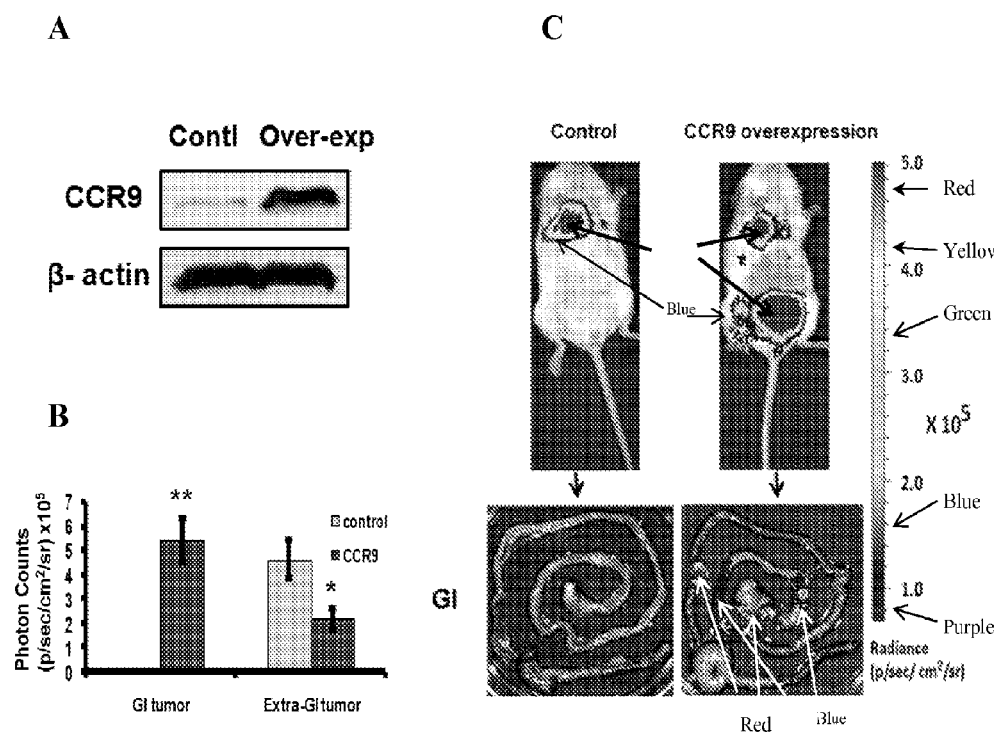
FIG. 10. CCR9 overexpression in HCT116 significantly increased GI tumor formation and reduced extra-GI tumor formation (A). Western blot of CCR9 expression in HCT116 cells transfected with control vector or CCR9 constitutive expression vector. β-actin is loading control. (B). Quantification of GI and extra-GI tumors in mice that have HCT116 cells transfected with either CCR9 overexpression or control vector (n=6) injected by tail vein. Xenograft tumors were quantified by luciferase—photon signals with Xenogen software. **P<0.001; *P<0.01 compared to the control group. Error bars indicate S.E.M. The whole-mouse (right upper panel) or an ex vivo GI (right down panel) representative imaging is shown in (C).
Figure 11:
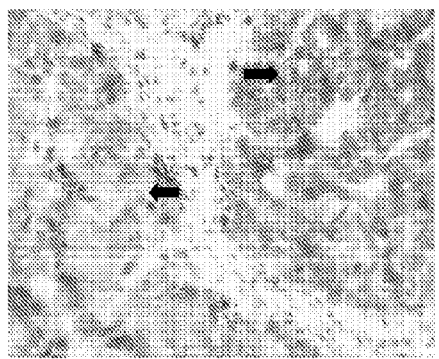
FIG. 11. CXCR4 expression in early stage CCIC extra-GI tumor. CXCR4 protein detected by immunohistochemistry in xenograft lung tumors, shown by DAB (A) IgG control; (B) anti-human CXCR4 antibody.
Figure 11:
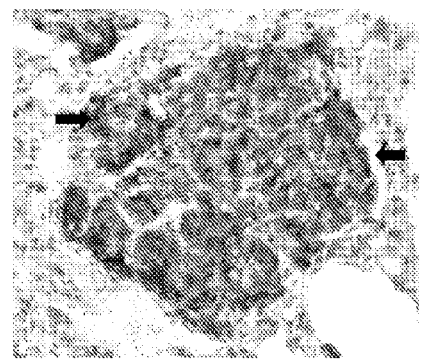

The CCR9/CCL25 axis regulates CCIC metastasis out of the GI tract. To understand whether CCR9/CCL25 regulates CCIC metastasis out of the GI tract, three sets of experiments involving antagonism of CCL25/CCR9 signaling after GI tumor initiation were performed. First, we injected mice with CCR9+ CCIC, waited 3 weeks for colon/intestinal tumors to form and then treated mice with anti-Ccl25 antibodies. This significantly increased both the incidence and multiplicity of CCIC ex-GI tumors (Table 3, FIG. 7D, FIG. 8, and FIG. 9B). Second, CCR9+ CCIC was injected with doxycycline inducible expression of anti-CCR9 or control shRNA. Approximately 3 weeks after injection, doxycycline was administered to induce CCR9 knockdown. This also significantly increased ex-GI CCIC tumor incidence and multiplicity (Table 3, FIG. 7, FIG. 8, and FIG. 9B). Third, HCT116 (which are CCR9−) sub-lines that stably express CCR9 (HCT116$^{CCR9+}$) were created and IVIS imaging was used to monitor the sites of tumor formation after tail vein injection. While HCT116 cells form ex-GI tumors, HCT116$^{CCR9+}$ cells in contrast form GI tumors in addition to ex-GI tumors. Interestingly, stable expression of CCR9 also reduces the overall burden of ex-GI tumors, as quantified by IVIS photon counting (FIG. 10). Altogether, these studies are consistent with CCL25/CCR9 antagonism causing CCIC in the intestine and colon to migrate outside the GI microenvironment and form additional ex-GI tumors.

Figure 6:
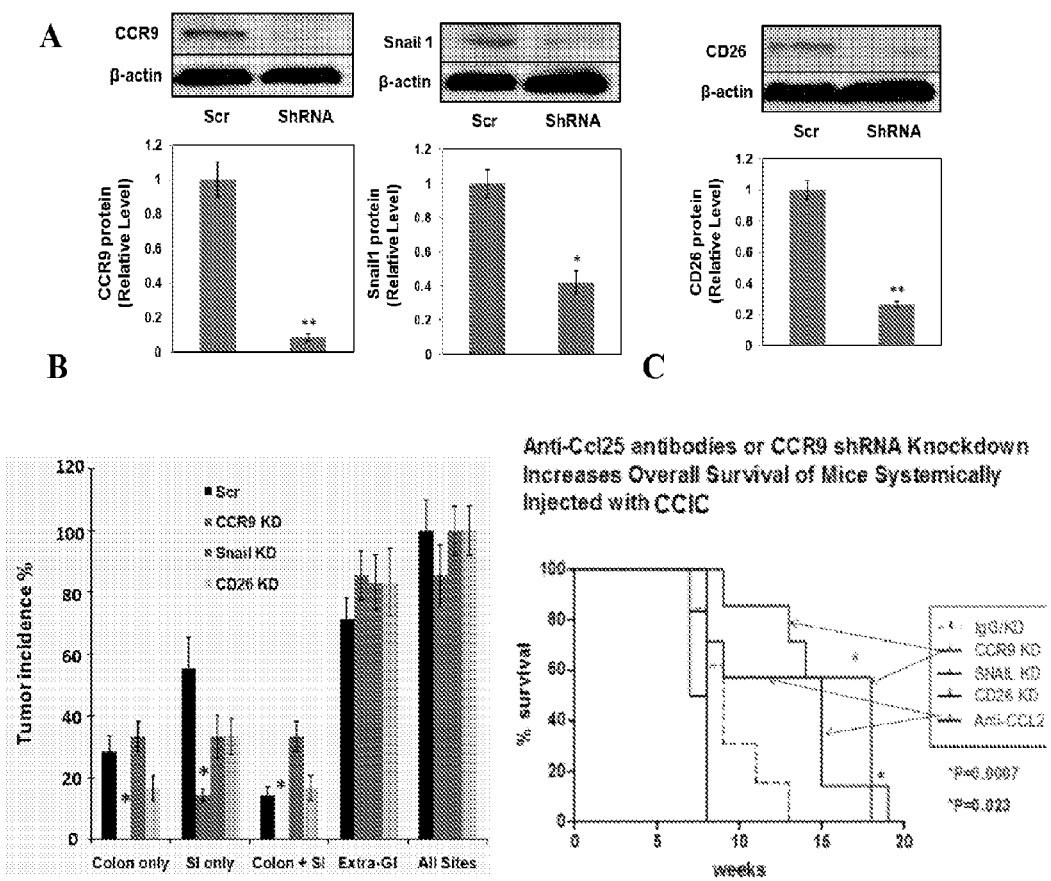
FIG. 6. Anti-Ccl25 antibody systemic injection or shRNA knockdown of CCR9, but not CD26 or SNAIL, increases survival of mice systemically injected with CCIC. (A) shRNA constitutive knockdown efficiencies of CCR9, CD26 or SNAIL in CCIC were tested by western (left) and quantified (right) by using western quantification software of Quantitity One (BioRad). (B) Xenograft tumor incidence in mice injected with CCIC expressing anti-CCR9, SNAIL1 or CD26 shRNA knockdown, organized by tumor site. *P<0.01 compared to scrambled shRNA control. Error bars indicate S.E.M.

CD26 and SNAL1 are associated with colorectal cancer migration and metastasis. To understand whether they could play a role in CCIC migration outside the GI tract, shRNA to knock down expression of CD26 or SNAL1 by ~70% was used (FIG. 6A). However, neither of these gene knockdowns affected colon/intestine or ex-GI CCIC tumor formation, or survival of mice systemically injected with CCIC (FIG. 6 B, C.).

The commonly used colorectal cancer cell lines tested express little or no CCR9. When injected systemically in mice, some lines can form tumors outside the GI tract. However, no spontaneous orthotopic colon/intestine tumor formation has ever been reported previously with any colorectal cancer cell line. This reflects their long term in vitro culture in the absence of CCL25.

Since our novel in vivo orthotopic CRC tumor formation system models the transition directly from GI-localized neoplasms to metastatic carcinomas, the CCIC lines described here have the potential to be a useful model to identify important "driver" mutations, epigenetic changes and signaling pathways that regulate pre-invasive to invasive and metastatic CRC progression, with less confounding by the high background "passenger" mutation rates seen in advanced CRC tumors. Functional CCR9 responsive to CCL25 is expressed by multiple tumor types, including prostate, ovarian, breast and pancreatic adenocarcinomas and melanomas.

The following materials and methods were used to obtain the data presented and discussed above.

Histology and Immunohistochemistry Representative sections from patient CRC specimens were immunostained for CCR9 using a 1:150 dilution of anti-human CCR9 (Abcam #ab38564) with antigen retrieval and peroxidase-based detection. Cases varied in clinical stage from in situ carcinomas (Tis) to transmural involvement (T4). For each case, CCR9 staining intensity was assessed (range 0-3) for normal crypt epithelium, and neoplastic tissue from each involved layer of the colon wall using double blank scoring method. Intensity±S.E.M. is shown.

Cell Culture. AJCC clinical stage I/II (referred to here as early) and stage III/IV (late) CCIC lines were generated using colon cancer "stem" cell culture conditions of Vermeulen et al with several modifications as previously described. Briefly, CRC patient fresh primary and metastatic tumor biospecimens were extensively washed with PBS, minced, and incubated at 37° C. with collagenase. Cells were then strained through 40-μm filter and cultured as "colonospheres". Colonospheres were cultured in ultralow-attachment flasks in DMEM/F12 containing nonessential amino acids penicillin (500 U/ml), streptomycin (500 mg/ml), and amphotericin B (1.25 mg/ml) and heparin (4 μg/mL; Sigma). Changes from included increased concentrations of epidermal growth factor (40 ng/mL), and basic fibroblast growth factor (20 ng/mL) and the addition of B27 supplement (Invitrogen). Cells were incubated at 37° C. and 5% CO2. Cells were cloned as single cells, expanded and frozen in DMSO. With these conditions clonal cultured colonospheres were considered to be CCIC based on the following criteria: (1) 50+% FACS positive status for CD44, CD133 and ALDH1 (tested individually), (2) 1:1,000-1:10,000 cell ability to form subcutaneous xenografts in NOG mice, (3) capable of serial self-renewal in sub-cutaneous xenografts assays, (4) ability to form subcutaneous xenograft tumors with adenocarcinoma histomorphology. Additionally, CCIC were also noted to express LGR5, NOTCH 1,2 receptors, JAG1, DLL4 and nuclear β-catenin (consistent with expression of WNT target genes such as CD44 and LGR5). CCR9/ALDH1 co-expressing cells are also observed.

Primary CRC culture. Primary CRC culture used the method of collagenase/dispase enzyme digestion with slight modification. Fresh samples of CRC were collected in DMEM/F12 supplemented with 10% FBS and 2% penicillin/streptomycin, immediately after patient operative resection. Tissue was dissected free of fat and blood clots and rinsed 5 times with PBS supplemented with 2% penicillin/streptomycin. Then tissue was minced into approximately 1 mm fragments and digested in DMEM/F12 containing collagenase type XI (150 U/ml, Sigma, St. Louis, Mo.), dispase neutral protease (40 μg/ml, Roche Applied Science) and 1% FBS, stirring at 37° C. for 30 min. After centrifugation, cells were re-suspended in the CCIC culture medium containing 5% FBS, 1% penicillin/streptomycin and cultured in the ultra-low-attachment flashes for a short time (1-2 passages), then the cell culture was shifted into complete CCIC medium without FBS. FACS with ESA was used to purify CRC and cells within 5 passages were used for following experiments.

CCR9 constitutive and inducible knockdown; Snail or CD26 knockdown in CCIC and NOTCH reporter CCIC. The lentiviral vector pEco-CMV-H1-shRNA-GFP encoding a shRNA hairpin sequence (CCR9: 5'-CTTGTACTG-GCTCGTGTTCAT SEQ ID NO:14; Snail: 5'-GAGCTGCA-GGACTCTATCCA SEQ ID NO:15; CD26: 5'-CATTCCTA-CACAGCTTCATAT SEQ ID NO:16) was used for CCR9, Snail or CD26 expression knockdown and the lentiviral vectors pEco-CMV-H1-GFP (GenTarget Inc, San Diego, Calif.) and pEco-CMV-H1-scrambled-shRNA-GFP served as controls. To generate the lentiviral vectors, the above plasmids were transfected into HEK293T cells with the Genetargetlentivirus packaging mix (GenTarget Inc, San Diego, Calif.) according to the manufacturer's protocol. For CCR9 tetracycline inducible knockdown, the same shRNA hairpin sequence against CCR9 gene was inserted into pLenti-H1-shRNA-RSV (GFP-Puro) vector (GenTarget Inc, San Diego, Calif.) and packaged into lentivirus particles, which were used together with another TetR expression lentivirus (RFP-Bsd)(GenTarget Inc, San Diego, Calif.) to infect CCICs. After antibiotic selection and GFP/RFP dual FACS purification, the CCR9 shRNA knockdown can be induced by 1 ug/ml (in vitro) or 1 mg/ml (in vivo) doxycycline. NOTCH signaling reporter CCIC was generated by infecting CCIC with pCignalLenti RBP-Jk Reporter (GFP) ready lentivirus (SABiosciences, Inc.). After infecting CCIC lines with these lentiviral vectors, stable knockdown clones were obtained through antibiotic selection of blasticidin (Invitrogen, Carlsbad, Calif.). The efficiency of the CCR9, SNAIL or CD26 knockdown in CCIC was verified by Western Blotting and efficiency of NOTCH signaling reporter was tested by 2 μg/ml Jagged-1 (AnaSpec) treatment following by GFP-FACS sorting.

CCIC xenograft tumor formation in colon/intestine and other organs. 0.5-1×10$^6$CCIC or common CRC cells were injected into 6-8 weeks old non-obese diabetic/severe combined immunodeficient (NOD/SCID) mice (Jackson Laboratory, Bar Harbor, Me.) by tail vein injection. Tumor incidence was monitored 2-3× weekly. When mice became moribund, they were sacrificed immediately, necropsy performed and tumors harvested using a dissecting microscope. For ex vivo GFP imaging of tumor tissues, lentiviral infection by the pEco-CMV-GFP vector was used to generate CCIC lines that stably express GFP and maintained in puromycin selection. 10$^6$ of these fluorescent CCIC were systemically injected as described above. Intestinal tissues harvested at the time of sacrifice were analyzed for GFP expression with Cri Maestro Imaging Systems (Cambridge Research & Instrumentation Inc, Woburn, Mass.).

For the CCR9 study, native CCICs, CCICs with CCR9, Snail (SNAL1) or CD26 knockdown (or commonly used CRC cell lines such as HCT116, etc. as indicated), CCR9+ CCIC with CCR9 inducible knockdown were intravenously inoculated into the 6-8 weeks old NOD/SCID mice by tail vein. Mice that became moribund were sacrificed immediately, whereas the rest were closely monitored for 16 weeks before sacrifice. To test whether CCL25 antibody could inhibit the CCL25-CCR9 GI homing mechanism in vivo, a dose of 100 ug goat anti-mouse CCL25 neutralization antibody (R&D systems, Cat #AF-481-NA), was IP administrated to each mouse twice (the same dose and schedule as used in). As a negative control, a dose of 100 ug Goat IgG (R&D systems) was administered to each mouse in the control group. Then 1×10$^6$CCIC were injected into the mice 8 hours after or with the injection of the antibody. To test whether extra-GI metastasis is induced by CCR9/CCL25 signaling blockade, CCL25 neutralization antibody with the same dose was IP administrated to each mouse every three days or 1 mg/ml doxycycline in drinking water was given to mice every other days starting from the fourth week after CCIC inoculation until mice get moribund.

Genomic DNA extraction and semi-quantitative PCR. Genomic DNA from CCIC culture, lung and intestinal adenomas normal tissues, or mouse tail was extracted using a tissue DNA extraction kit (Qiagen, Valencia Calif.). Semi-quantitative PCR was done followed by DNA gel electrophoresis. Human centromeric repeat loci were used as markers to detect human cells in harvested mouse tissues. Primer sequence pairs used are (1) 5'-GAGTGCACATTCA-GACAAGACCC-3' (SEQ ID NO:4) and 5'-CCATTAGA-GAGCTTTCCTCATTGC-3'(SEQ ID NO:5) or (2) 5'-CGT-GTGTTTTTGGTTACTTCTCCCC-3' (SEQ ID NO:6) and 5'-CTTAGCCATTGCCCATTGATGGA-3' (SEQ ID NO:7).

Quantitative real-time PCR. Total RNAs from cells were extracted by using RNeasy Kit (Qiagen, Valencia Calif.). 2 μg of total RNAs were reverse-transcribed into cDNA by using RT first stand kit (SA Biosciences) and RNA levels, normalized to GAPDH as the comparative CT (cycling threshold)=CT (target)–CT (control), were analyzed by the iCycler (Bio-Rad). Primer pairs used are (1) GAPDH 5'-ACAGTCAGCCGCATCTTCTT-3' (SEQ ID NO:8) and 5'-AATGAAGGGGTCATTGATGG-3'; (SEQ ID NO:9) (2) HES 15'-ACGACACCGGATAAACCAAA-3' (SEQ ID NO:10) and 5'-CGGAGGTGCTTCACTGTCAT-3'; (SEQ ID NO:11) (3) CCR9 5'-CACAGACTTCACAAGCCCTA-3 (SEQ ID NO:12) and 5'-GTACAAGGGTGGGAGGAAAT-3' (SEQ ID NO:13).

Transwell migration assay. Transwell Boyden chambers (BD Pharmingen Mountain View, Calif.) of 8-μm pore size were used to evaluate primary CRC cell and CCIC migration in vitro. Primary CRC cells or CCICs were seeded at a density of 5×10$^5$ per well into the upper chamber. CCIC culture medium as described above with 100 ng/ml recombinant mouse CCL25 protein (R&D systems Inc; Minneapolis, Mass.) or 5% FBS was loaded into the lower chamber. Chambers of cells were incubated in 37° C. and 5% $CO_2$ conditions for 8-12 hours. At the time of harvest, cells remaining inside the upper chambers were removed while cells attached to the lower surface of the membrane were fixed and stained with hexamethylpararosaniline chloride (Crystal violet) (Sigma, St Louis, Mo.) or immunofluorescence staining with anti-CCR9 or CEA antibodies, followed by imaging analyses.

SmartChip RT-PCR Procedures and Functional Analysis. Early stage CCIC were FACS sorted into CCR9+ and CCR9− subpopulations. 24 hours afterwards, cells were treated with 100 ng/ml human CCL25 for 30 min. RNA was extracted from both populations using PureLink RNA Mini kit (Invitrogen) and analyzed using the SmartChip Real-Time PCR System (WaferGen Biosystems, Fremont, Calif.). Briefly, cDNA was prepared using 1 ug of total RNA per sample per manufacturer's recommendation. A PCR cocktail containing SYBR Green I dye and the equivalent of 1000 ng of starting RNA for each sample was loaded onto the SmartChip Human Oncology V2 Panel (containing 1,296 unique real-time PCR reactions in quadruplicate for a total of 5,184 reactions/sample). The volume was 100 nL with an equivalent of 96 pg of RNA loaded per reaction. Forty cycles of real-time PCR were performed on the SmartChip Cycler collecting both raw Ct and Tm of each gene and sample for data analysis. A data quality screen on amplification, Tm curves, and Ct and Tm variability was performed to remove any outlier data. All-means normalization was performed on quadruplicate PCRs and delta-delta Ct calculations were used to determine fold change in expression. Genes either with a log 2 fold change by a factor of greater than 1.8 (that correlates to ~3.3 fold or higher), or expressed in only one sample with min raw of Ct of 24.99 were deemed significantly differentially expressed between CCR9− and CCR9+ early stage CCIC cells.

Statistics Summary. All experiments were done with four to eight samples per group, unless otherwise indicated, and all results were derived from at least five independent experiments. Values are expressed as mean±SEM. For Student's t test, a 2-tailed test was used.

A p value less than 0.05 was considered significantly. Statistical calculations were performed with the Statistical Package for the Social Sciences version 11.5 software (SPSS Inc, Chicago, Ill.) or GraphPad. The statistical test used for each figure or table panel is indicated.

TABLE 1

CCIC and common CRCs form orthotopic xenograft tumors in mouse intestine, colon and other sites. colon/intestine and ex-GI tumors from mice injected with cells by tail vein. Asterisks denote statistically significant differences among CRC cell lines SW480 and LoVo, early and late stage CCIC as determined by one way ANOVA.

| Cells | # Mice | Mean Progression (weeks) | GI Tumor Incidence (%) | Mean GI Tumors/ mouse | Ex-GI Tumor Incidence (%) | Mean Ex-GI Tumors/Mouse |
|---|---|---|---|---|---|---|
| Early Stage CCIC | 62 | 8.6 | 73.3 | 3.7 | 35.6 | 126.0 |
| Late Stage CCIC | 11 | 6.5* | 0* | 0* | 91.0* | 71.1* |
| Non-CCIC CRC lines | 24 | 11.8* | 0* | 0* | 20.0* | 66.2* |

*$P < 0.01$ compared to early stage CCICs.

TABLE 2

CCR9/CCL25 is required for CCIC colon/intestine tumor formation. mice injected with early stage CCIC. Rows 1-2: Mice injected with CCR9+ CCIC or CCR9− CCIC (*$P < 0.001$ for Row 1-2 comparison). Rows 3-4: Anti-Ccl25 antibody reduces GI tumor incidence (*$P < 0.05$ for row 3-4 comparison). Rows 5-6: CCR9 shRNA lentiviral knockdown (KD) reduces GI tumor incidence and multiplicity, and increases ex-GI multiplicity (*$P < 0.01$ for row 5-6 comparison).

| Cells | # Mice | Mean Progression (weeks) | GI Tumor Incidence (%) | Mean GI Tumors/ mouse | Ex-GI Tumor Incidence (%) | Mean Ex-GI Tumors/Mouse |
|---|---|---|---|---|---|---|
| CCR9+ | 8 | 9.4 | 75.0* | 3.8* | 25.0 | 8.3* |
| CCR9− | 8 | 10.0 | 12.5 | 0.25 | 87.5 | 75.6 |
| Anti-CCL25 [a] (Pre-injection) | 6 | 11.3 | 28.5 | 1.1* | 100.0 | 95.9 |
| Control IgG | 6 | 9.2 | 83.3 | 3.0 | 83.3 | 77.5 |
| CCR9 KD [b] | 7 | 13.0* | 14.3* | 0.3* | 85.7 | 105.0* |
| Control shRNA | 7 | 9.6 | 100.0 | 3.7 | 71.4 | 82.5 |

[a] anti-CCL25 (pre-injection) means mice were IP injected with anti-CCL25 neutralization antibody before and concurrent with CCSC tail vein injection.
[b] CCIC with CCR9 shRNA knockdown were tail vein injected in mice.

TABLE 3

BlockingCCR9/CCL25 signaling after intestinal tumor formation increases metastasis. Mice injected with early stage CCIC. Top, after three weeks to allow GI tumors to form from injected CCR9+ early stage CCIC, mice were IP injected with 100 μg/mouse goat anti-mouse CCL25 neutralization antibody or goat control IgG every three days until moribund. The mice in anti-CCL25 groups formed extra-intestinal metastatic tumors in abdominal tissues, pancreas, kidney and liver (*$P < 0.001$ statistically significant different to goat control IgG treatment, row 2). Bottom, after 3 weeks to allow GI tumors to form from injected CCR9+ early stage CCIC carrying either doxycycline regulatable anti-CCR9 or control shRNA, 1 mg/ml doxycycline in drinking water was given to the mice every other day until moribund to induce CCR9 knockdown in tumor cells. The mice with inducible CCR9 knockdown formed extra-intestinal metastatic tumors in abdominal tissues, pancreas, kidney and liver (*$P < 0.001$). Also see FIGS. 6 and 7.

| Cells | # Mice | Mean Progression (weeks) | GI Tumor Incidence (%) | Mean GI Tumors/ mouse | Ex-GI Tumor Incidence (%) | Mean Ex-GI Tumors/Mouse |
|---|---|---|---|---|---|---|
| Anti-CCL25[a] (post injection) | 7 | 7.9 | 71.4 | 2.4 | 42.8* | 2.9* |
| Control IgG | 7 | 8.7 | 85.7 | 3.3 | 0 | 0 |
| CCR9 [b] Inducible KD | 8 | 8.1 | 62.5 | 2.2 | 50.0* | 3.4* |
| Control shRNA | 8 | 8.9 | 87.5 | 3.2 | 12.5 | 0.2 |

[a] anti-CCL25 (post injection) means mice were IP injected with anti-CCL25 neutralization antibody three weeks after CCR9+ CCIC tail vein injection.
[b] CCR9+ CCIC with CCR9 inducible shRNA were tail vein injected in mice and CCR9 knockdown were generated in vivo by administration of doxycycline three weeks later.

Immunohistochemistry For mouse experiments, histology and immunohistochemistry were performed on paraffin-embedded or frozen sections from xenograft tumors. Intestinal, extra-GI tumor and corresponding normal tissues were snap frozen in OCT (Fisher Scientific, Pittsburgh, Pa.) and fixed in 10% buffered formalin followed by paraffin embedding. For immunofluorescence, sections were immunostained with antibodies, counterstained with 4,6-diamidino-2-phenylindole (DAPI). H+E adjacent sections were used for comparison.

Immunocytochemistry. Cells were fixed with mixture of acetone and methanol (1:1) at −20° C. for 20 min, then rinsed three times with PBS. Following cells were incubated in a blocking solution (5% BSA or normal serum (goat, rabbit or horse) and 0.1% Triton-X in PBS) for 1 hour. For single or co-immunofluorescence staining, primary antibodies diluted in blocking solution were added overnight at 4° C. overnight. To ensure specificity, a no primary antibody control staining was performed. The slides were then washed in PBS and incubated with the appropriate secondary antibody for 1 hour at room temperature and counterstained/mounted with Vectashield containing DAPI (Vector Laboratories). Images were acquired on an inverted fluorescence microscope (Nikon Eclipse E800, Morrell Instruments). Ariol SL-50 imaging software (Applied Imaging Instruments) was used to quantify biomarker staining. At least n=100 cells from three independent staining experiments were analyzed. Data are presented as means±SEM and the significance was tested with the Student t test.

Fluorescent activated cell sorting (FACS) analysis FACS with anti-epithelial specific antigen (ESA, BD Pharmingen #347197) antibody was used to purify primary CRC cells or with anti-CCR9 antibody (BD Pharmingen Mountain View, Calif.) to sort CCR9+ and CCR9− CCIC. Cells were first incubated with anti-human CCR9 antibody for 30 minutes on ice and then were washed in 1% BSA/PBS buffer. FACS was then used to separate CCIC into CCR9 positive and negative sub-groups by signal intensity gating. Approximately 6-8 hours after sorting, CCR9+ and CCR9− subsets from $1\times10^6$ CCIC were inoculated into two mice by tail vein injection and monitored as described above. GFP-NOTCH FACS sorting was performed as described (44).

Western Blotting. Isolated mouse intestine, lung tissues, cultured CCIC, or ATCC CRC cell lines were homogenized in RIPA buffer and complete protease inhibitor cocktail (Roche Applied Science, Indianapolis, Ind.)] with brief sonication on ice, and centrifuged for 5 minutes at 14,000 r.p.m to remove large debris. Protein concentration of the supernatant was determined by Bradford protein assay (Bio-Rad Laboratories Inc, Hercules, Calif.). Fifty micrograms of protein derived from tissue or cell lysates were separated by SDS-PAGE and transferred to polyvinylidenedifluoride membranes. Following blocking, membranes were probed with primary antibodies to determine different levels of protein expressions. Specific antibodies targeting CCR9 (Abcam, Cambridge, Mass.), CCL25 (R&D systems Inc; Minneapolis, Mass., Cat #AF-481-NA), AKT (Cell Signaling, Inc, Cat #9272), phospho-AKT (ser 473, Cell Signaling, Inc, Cat#9271), phospho-AKT (thr 308, Cell Signaling, Inc, Cat #9275), GSK-3β (Cell Signaling, Inc, Cat #9315), phosphor-GSK-3β (Cell Signaling, Inc, Cat #9336), NICD (R&D Systems, Cat #AF3647), HES1 (Santa Cruz, Cat #sc-13842), Snail (Cell Signaling, Cat #3879), CD26 (Calbiochem, Cat #IM1004) were used, and anti-actin antibody (Santa Cruz Biotechnology Inc, Santa Cruz, Calif., Cat #sc-1616-R) was used as internal controls Immunoreactive antibody-antigen complexes were visualized with the enhanced chemiluminescence reagents from GE Healthcare (Uppsala, Sweden). The software of Quantity One (BioRad) was used to semi-quantify protein levels in western.

Generation of CCR9 constitutive expression CRC line. The SureTiter™ lentivector (GenTarget Inc, San Diego, Calif.) in which the sub-cloned human CCR9 ORF sequence (gene ID: NM_006641) and a firefly luciferase gene were under control of CMV promoter was used to generate constitutively CCR9 expressing cell lines. To generate the lentiviral particles, the above plasmids were transfected into HEK293T cells with the Genetarget lentivirus packaging mix (GenTarget Inc, San Diego, Calif.) according to the manufacturer's protocol. The common used CRC line HCT116 was infected with lentivirus and positive cells selected by antibiotic.

Luciferase imaging in whole animal or ex vivo tissues: Each NOG mouse was tail vein injected with $0.5\times10^6$ CCR9 constitutively expressing or scrambled control HCT116 cells and tumor formation was determined by luciferase-IVIS imaging system every 3 days For luciferase imaging, D-luciferin of 1.5 mg/10 g body weight was intra-peritoneally injected into mice and 10 min later, luciferase imaging (Xenogen IVIS-200) was applied on whole-mouse body or ex vivo tissues.

Cell proliferation assay. CCR9+ primary CRC and CCIC were FACS sorted and seeded in ultro-low attachment 24-well plates for 12 hours. 100 ng/ml human CCL25, 1 μg/ml CCR9 neutralizing antibody (R&D systems Inc), 2 μM pan-AKT inhibitor Triciribine (Sigma) or control goat IgG were added into culture medium and cells were continued to incubate for 36 hours. The cellular ATP (adenosine triphosphate) levels were measured to quantify cell proliferation and viability using the ViaLightPlus Kit (Lonza Rockland, Inc.) and GloMax-20/20 Single-Tube Luminometer (Promega) per manufacture instructions.

All experiments were done with four to eight samples per group, unless otherwise indicated, and all results were derived from at least five independent experiments. Values are expressed as mean±SEM. For Student's t test, a 2-tailed test was used.

A p value less than 0.05 was considered significantly. Statistical calculations were performed with the Statistical Package for the Social Sciences version 11.5 software (SPSS Inc, Chicago, Ill.) or GraphPad. The statistical test used for each figure or table panel is indicated.

TABLE 4

Primary human colorectal cancers used for CCR9 FACS, chemotaxis, p-AKT and cell proliferation analyses

| ID | Age | Gender | Stage | Histopathology | Assays[a] |
|----|-----|--------|-------|----------------|-----------|
| 1 | 81 | M | I | Adenocarcinoma, moderately differentiated | FACS/ p-AKT/ chemotaxis |
| 2 | 74 | M | I | Adenocarcinoma, moderately differentiated | FACS/ p-AKT/ chemotaxis |
| 3 | 70 | F | I | Adenocarcinoma, well to moderately differentiated | FACS/ p-AKT/ chemotaxis |
| 4 | 86 | F | II | Adenocarcinoma, well to moderately differentiated | FACS/ chemotaxis |
| 5 | 58 | M | II | Adenocarcinoma, well to moderately differentiated | FACS/ chemotaxis |

TABLE 4-continued

Primary human colorectal cancers used for CCR9 FACS, chemotaxis, p-AKT and cell proliferation analyses

| ID | Age | Gender | Stage | Histopathology | Assays[a] |
|---|---|---|---|---|---|
| 6 | 63 | M | I | Adenocarcinoma, well to moderately differentiated | FACS/chemotaxis |
| 7 | 59 | F | II | Adenocarcinoma, poorly differentiated | FACS/chemotaxis |
| 8 | 90 | F | II | Adenocarcinoma, poorly differentiated | FACS/Proliferation |
| 9 | 85 | M | I | Adenocarcinoma, poorly differentiated | FACS/Proliferation |
| 10 | 40 | M | II | Adenocarcinoma, poorly differentiated | FACS |

[a]The primary CRC cells were used for the assays of FACS, chemotaxis function, AKT phospholation or cell proliferation.

TABLE 5

Colorectal Cancer Initiating Cell Lines used for multiple analyses

| ID | Age | Gender | Stage | Histopathology | Assays[a] |
|---|---|---|---|---|---|
| (early stage) CCIC1 | 57 | M | I | Adenocarcinoma, well to moderately differentiated | FACS/Mouse/p-AKT/Chemotaxis/Proliferation/Western/Q-PCR/Microarray |
| (early stage) CCIC2 | 51 | M | II | Adenocarcinoma, well differentiated | FACS/Mouse/p-AKT/Chemotaxis/Proliferation/Western/Q-PCR |
| (early stage) CCIC3 | 74 | F | I | Adenocarcinoma, well to moderately differentiated | FACS/Mouse/Western |
| (late stage) CCIC1 | 54 | M | III | Adenocarcinoma, moderately differentiated | FACS/Mouse/Chemotaxis/Western |
| (late stage) CCIC2 | 61 | M | IV | Carcinoma, poor to moderately differentiated (liver metastasis) | FACS/Mouse/Western |

[a]The CCIC cells were used for the assays of FACS, in vivo mouse study, chemotaxis function, AKT phospholation, cell proliferation, western blot, quantative PCR, or microarray.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method for making a non-human mammal comprising an orthotopic tumor in its gastrointestinal tract that metastasizes to the lungs and/or liver comprising:

a) introducing into a non-human mammal a plurality of human Chemokine Receptor 9 positive (CCR9+) colorectal cancer cells, wherein subsequent to the introduction the human colorectal cancer cells form a tumor in the gastrointestinal tract of the non-human mammal, wherein the cancer cells contain an expression vector, wherein the expression vector comprises an inducible promoter that controls expression of an shRNA targeted to the human CCR9, the method further comprising inducing the expression of the shRNA such that the tumor metastasizes to the lungs and/or liver.

2. A non-human mammal comprising an orthotopic a tumor in its gastrointestinal tract that metastasizes to the lungs and/or liver made by the method of claim 1.

3. A method for determining whether a test agent is a candidate for inhibition of metastasis comprising providing a non-human animal of claim 2, allowing metastasis of the orthotopic tumor to the lungs and/or liver, and after a period of time measuring metastasis of the tumor to the lungs and/or liver, wherein a reduction of metastasis relative to a control indicates that the test agent is a candidate for use as an inhibitor of metastasis of the tumor to the lungs and/or liver.

* * * * *

SEQUENCE LISTING

<160> NUMBER OF SEQ ID NOS: 16

<210> SEQ ID NO 1
<211> LENGTH: 369
<212> TYPE: PRT
<213> ORGANISM: Human

<400> SEQUENCE: 1

```
Met Thr Pro Thr Asp Phe Thr Ser Pro Ile Pro Asn Met Ala Asp Asp
1               5                   10                  15

Tyr Gly Ser Glu Ser Thr Ser Ser Met Glu Asp Tyr Val Asn Phe Asn
                20                  25                  30

Phe Thr Asp Phe Tyr Cys Glu Lys Asn Asn Val Arg Gln Phe Ala Ser
            35                  40                  45

His Phe Leu Pro Pro Leu Tyr Trp Leu Val Phe Ile Val Gly Ala Leu
        50                  55                  60

Gly Asn Ser Leu Val Ile Leu Val Tyr Trp Tyr Cys Thr Arg Val Lys
65                  70                  75                  80

Thr Met Thr Asp Met Phe Leu Leu Asn Leu Ala Ile Ala Asp Leu Leu
                85                  90                  95

Phe Leu Val Thr Leu Pro Phe Trp Ala Ile Ala Ala Asp Gln Trp
            100                 105                 110

Lys Phe Gln Thr Phe Met Cys Lys Val Val Asn Ser Met Tyr Lys Met
        115                 120                 125

Asn Phe Tyr Ser Cys Val Leu Leu Ile Met Cys Ile Ser Val Asp Arg
    130                 135                 140

Tyr Ile Ala Ile Ala Gln Ala Met Arg Ala His Thr Trp Arg Glu Lys
145                 150                 155                 160

Arg Leu Leu Tyr Ser Lys Met Val Cys Phe Thr Ile Trp Val Leu Ala
```

```
                165                 170                 175
Ala Ala Leu Cys Ile Pro Glu Ile Leu Tyr Ser Gln Ile Lys Glu Glu
            180                 185                 190

Ser Gly Ile Ala Ile Cys Thr Met Val Tyr Pro Ser Asp Glu Ser Thr
            195                 200                 205

Lys Leu Lys Ser Ala Val Leu Thr Leu Lys Val Ile Leu Gly Phe Phe
            210                 215                 220

Leu Pro Phe Val Val Met Ala Cys Cys Tyr Thr Ile Ile His Thr
225                 230                 235                 240

Leu Ile Gln Ala Lys Lys Ser Ser Lys His Lys Ala Leu Lys Val Thr
            245                 250                 255

Ile Thr Val Leu Thr Val Phe Val Leu Ser Gln Phe Pro Tyr Asn Cys
            260                 265                 270

Ile Leu Leu Val Gln Thr Ile Asp Ala Tyr Ala Met Phe Ile Ser Asn
            275                 280                 285

Cys Ala Val Ser Thr Asn Ile Asp Ile Cys Phe Gln Val Thr Gln Thr
            290                 295                 300

Ile Ala Phe Phe His Ser Cys Leu Asn Pro Val Leu Tyr Val Phe Val
305                 310                 315                 320

Gly Glu Arg Phe Arg Arg Asp Leu Val Lys Thr Leu Lys Asn Leu Gly
            325                 330                 335

Cys Ile Ser Gln Ala Gln Trp Val Ser Phe Thr Arg Arg Glu Gly Ser
            340                 345                 350

Leu Lys Leu Ser Ser Met Leu Leu Glu Thr Thr Ser Gly Ala Leu Ser
            355                 360                 365

Leu

<210> SEQ ID NO 2
<211> LENGTH: 15
<212> TYPE: PRT
<213> ORGANISM: human

<400> SEQUENCE: 2

Lys Leu Ser Ser Met Leu Leu Glu Thr Thr Ser Gly Ala Leu Ser
1               5                   10                  15

<210> SEQ ID NO 3
<211> LENGTH: 2567
<212> TYPE: DNA
<213> ORGANISM: human

<400> SEQUENCE: 3 gcttccttc tcgtgttgtt atcgggtagc tgcctgctca gaacccacaa agcctgcccc      60
tcatcccagg cagagagcaa cccagctctt tccccagaca ctgagagctg gtggtgcctg    120
ctgtcccagg gagagttgca tcgccctcca cagagcaggc ttgcatctga ctgacccacc    180
atgacaccca cagacttcac aagccctatt cctaacatgg ctgatgacta tggctctgaa    240
tccacatctt ccatggaaga ctacgttaac ttcaacttca ctgacttcta ctgtgagaaa    300
aacaatgtca gcagtttgc gagccatttc ctcccaccct tgtactggct cgtgttcatc    360
gtgggtgcct tgggcaacag tcttgttatc cttgtctact ggtactgcac aagagtgaag    420
accatgaccg acatgttcct tttgaatttg gcaattgctg acctcctctt tcttgtcact    480
cttcccttct gggccattgc tgctgctgac cagtggaagt tccagacctt catgtgcaag    540
gtggtcaaca gcatgtacaa gatgaacttc tacagctgtg tgttgctgat catgtgcatc    600
```

```
agcgtggaca ggtacattgc cattgcccag gccatgagag cacatacttg gagggagaaa      660
aggcttttgt acagcaaaat ggtttgcttt accatctggg tattggcagc tgctctctgc      720
atcccagaaa tcttatacag ccaaatcaag gaggaatccg gcattgctat ctgcaccatg      780
gtttacccta gcgatgagag caccaaactg aagtcagctg tcttgacccct gaaggtcatt     840
ctggggttct tccttcccct cgtggtcatg gcttgctgct ataccatcat cattcacacc      900
ctgatacaag ccaagaagtc ttccaagcac aaagccctaa aagtgaccat cactgtcctg      960
accgtctttg tcttgtctca gtttccctac aactgcattt tgttggtgca gaccattgac     1020
gcctatgcca tgttcatctc caactgtgcc gtttccacca acattgacat ctgcttccag     1080
gtcacccaga ccatcgcctt cttccacagt tgcctgaacc ctgttctcta tgtttttgtg     1140
ggtgagagat tccgccggga tctcgtgaaa accctgaaga acttgggttg catcagccag     1200
gcccagtggg tttcatttac aaggagagag ggaagcttga agctgtcgtc tatgttgctg     1260
gagacaacct caggagcact ctccctctga ggggtcttct ctgaggtgca tggttctttt     1320
ggaagaaatg agaaatacag aaacagtttc cccactgatg ggaccagaga gagtgaaaga     1380
gaaaagaaaa ctcagaaagg gatgaatctg aactatatga ttacttgtag tcagaatttg     1440
ccaaagcaaa tatttcaaaa tcaactgact agtgcaggag gctgttgatt ggctcttgac     1500
tgtgatgccc gcaattctca aaggaggact aaggaccggc actgtggagc accctggctt     1560
tgccactcgc cggagcatca atgccgctgc ctctggagga gcccttggat ttctccatg      1620
cactgtgaac ttctgtggct tcagttctca tgctgcctct tccaaaaggg gacacagaag     1680
cactggctgc tgctacagac cgcaaaagca gaaagtttcg tgaaaatgtc catctttggg     1740
aaattttcta ccctgctctt gagcctgata acccatgcca ggtcttatag attcctgatc     1800
tagaacctttt ccaggcaatc tcagacctaa tttccttctg ttctccttgt tctgttctgg    1860
gccagtgaag gtccttgttc tgattttgaa acgatctgca ggtcttgcca gtgaacccct     1920
ggacaactga ccacacccac aaggcatcca agtctgttg gcttccaatc catttctgtg      1980
tcctgctgga ggttttaacc tagacaagga ttccgcttat tccttggtat ggtgacagtg     2040
tctctccatg gcctgagcag ggagattata acagctgggt tcgcaggagc cagccttggc     2100
cctgttgtag gcttgttctg ttgagtggca cttgctttgg gtccaccgtc tgtctgctcc     2160
ctagaaaatg ggctggttct tttggcccctc ttctttctga ggcccacttt attctgagga    2220
atacagtgag cagatatggg cagcagccag gtagggcaaa ggggtgaagc gcaggccttg     2280
ctggaaggct atttacttcc atgcttctcc ttttcttact ctatagtggc aacattttaa     2340
aagcttttaa cttagagatt aggctgaaaa aaataagtaa tggaattcac ctttgcatct     2400
tttgtgtctt tcttatcatg atttggcaaa atgcatcacc tttgaaaata tttcacatat     2460
tggaaaagtg cttttttaatg tgtatatgaa gcattaatta cttgtcactt tctttaccct    2520
gtctcaatat tttaagtgtg tgcaattaaa gatcaaatag atacatt                   2567
```

<210> SEQ ID NO 4
<211> LENGTH: 23
<212> TYPE: DNA
<213> ORGANISM: artificial sequence
<220> FEATURE:
<223> OTHER INFORMATION: primer

<400> SEQUENCE: 4

```
gagtgcacat tcagacaaga ccc                                               23
```

```
<210> SEQ ID NO 5
<211> LENGTH: 24
<212> TYPE: DNA
<213> ORGANISM: artificial sequence
<220> FEATURE:
<223> OTHER INFORMATION: primer

<400> SEQUENCE: 5
ccattagaga gctttcctca ttgc                                              24

<210> SEQ ID NO 6
<211> LENGTH: 25
<212> TYPE: DNA
<213> ORGANISM: artificial sequence
<220> FEATURE:
<223> OTHER INFORMATION: primer

<400> SEQUENCE: 6
cgtgtgtttt tggttacttc tcccc                                             25

<210> SEQ ID NO 7
<211> LENGTH: 23
<212> TYPE: DNA
<213> ORGANISM: artificial sequence
<220> FEATURE:
<223> OTHER INFORMATION: primer

<400> SEQUENCE: 7
cttagccatt gcccattgat gga                                               23

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
acagtcagcc gcatcttctt                                                   20

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9
aatgaagggg tcattgatgg                                                   20

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10
```

```
acgacaccgg ataaaccaaa                                              20

<210> SEQ ID NO 11
<211> LENGTH: 20
<212> TYPE: DNA
<213> ORGANISM: artificial sequence
<220> FEATURE:
<223> OTHER INFORMATION: primer

<400> SEQUENCE: 11
cggaggtgct tcactgtcat                                              20

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
cacagacttc acaagcccta                                              20

<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
gtacaagggt gggaggaaat                                              20

<210> SEQ ID NO 14
<211> LENGTH: 21
<212> TYPE: DNA
<213> ORGANISM: artificial sequence
<220> FEATURE:
<223> OTHER INFORMATION: primer

<400> SEQUENCE: 14
cttgtactgg ctcgtgttca t                                            21

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
gagctgcagg actctatcca                                              20

<210> SEQ ID NO 16
<211> LENGTH: 21
<212> TYPE: DNA
<213> ORGANISM: artificial sequence
<220> FEATURE:
<223> OTHER INFORMATION: primer

<400> SEQUENCE: 16
cattcctaca cagcttcata t                                            21
```